(12) United States Patent
Karmeli et al.

(10) Patent No.: US 12,097,136 B2
(45) Date of Patent: Sep. 24, 2024

(54) GRAFT SECURING SYSTEM, APPLICATOR AND METHOD

(71) Applicant: Endoron Medical Ltd., Kfar Saba (IL)

(72) Inventors: Ron Karmeli, Haifa (IL); Eyal Teichman, Hod HaSharon (IL)

(73) Assignee: Endoron Medical Ltd., Kfar Saba (IL)

( * ) Notice: Subject to any disclaimer, the term of this patent is extended or adjusted under 35 U.S.C. 154(b) by 919 days.

(21) Appl. No.: 17/120,179

(22) Filed: Dec. 13, 2020

(65) Prior Publication Data

US 2021/0093313 A1    Apr. 1, 2021

Related U.S. Application Data

(63) Continuation of application No. PCT/IL2019/050664, filed on Jun. 12, 2019.

(51) Int. Cl.
*A61F 2/07* (2013.01)
*A61B 17/064* (2006.01)
*A61F 2/848* (2013.01)

(52) U.S. Cl.
CPC ............ *A61F 2/848* (2013.01); *A61B 17/064* (2013.01); *A61F 2/07* (2013.01); *A61B 2017/0645* (2013.01); *A61F 2002/8483* (2013.01); *A61F 2220/0008* (2013.01); *A61F 2220/0016* (2013.01)

(58) Field of Classification Search
CPC .... A61F 2/484; A61F 2002/8483; A61F 2/07; A61F 2220/0016
See application file for complete search history.

(56) References Cited

U.S. PATENT DOCUMENTS

| 4,586,923 A | 5/1986 | Gould et al. |
|---|---|---|
| 4,747,899 A | 5/1988 | Hasegawa |
| 5,151,105 A | 9/1992 | Kwan-Gett |

(Continued)

FOREIGN PATENT DOCUMENTS

| CN | 101394815 | 3/2009 |
|---|---|---|
| CN | 104055604 | 9/2014 |

(Continued)

OTHER PUBLICATIONS

Relatório de Busca e Parecer [Search Report and Opinion] Dated May 23, 2023 From the Serviço Público Federal, Ministério da Economia, Instituto Nacional da Propriedade Industrial do Brasil Re. Application No. BR 11 2020 024996 3 and Its Translation Into English. (7 Pages).

(Continued)

*Primary Examiner* — Suba Ganesan
(74) *Attorney, Agent, or Firm* — Greenberg Traurig, LLP; Christopher C. Bolten; Albert K. Heng

(57) ABSTRACT

A graft securing system including at least one expandable frame moveable from a collapsed state to an expanded state, and at least one anchor coupled to the frame via an elastic support strut, said anchor including: an anchor base, at least one deflectable prong protruding from said anchor base and having at least one penetration tip and at least one restraining sleeve at least partially slideably moveable along the at least one prong and wherein in the collapsed state, the support strut is biased radially centrally bringing the at least one anchor to point generally axially, parallel to a longitudinal axis of the frame.

20 Claims, 12 Drawing Sheets

(56) References Cited

U.S. PATENT DOCUMENTS

| | | | |
|---|---|---|---|
| 5,195,968 | A | 3/1993 | Lundquist et al. |
| 5,207,695 | A | 5/1993 | Trout, III |
| 5,415,664 | A | 5/1995 | Pinchuk |
| 5,906,590 | A | 5/1999 | Hunjan et al. |
| 6,551,302 | B1 | 4/2003 | Rosinko et al. |
| 6,592,593 | B1 | 7/2003 | Parodi et al. |
| 6,767,359 | B2 | 7/2004 | Weadock |
| 6,800,081 | B2 | 10/2004 | Parodi |
| 6,960,217 | B2 | 11/2005 | Bolduc |
| 7,025,779 | B2 | 4/2006 | Elliott |
| 7,128,754 | B2 | 10/2006 | Bolduc |
| 7,267,685 | B2 | 9/2007 | Butaric et al. |
| 7,326,231 | B2 | 2/2008 | Phillips et al. |
| 7,491,232 | B2 | 2/2009 | Bolduc et al. |
| 7,544,198 | B2 | 6/2009 | Parodi |
| 7,637,932 | B2 | 12/2009 | Bolduc et al. |
| 7,682,390 | B2 | 3/2010 | Seguin |
| 7,959,663 | B2 | 6/2011 | Bolduc |
| 7,959,670 | B2 | 6/2011 | Bolduc |
| 8,075,570 | B2 | 12/2011 | Bolduc et al. |
| 8,083,752 | B2 | 12/2011 | Bolduc |
| 8,092,519 | B2 | 1/2012 | Bolduc |
| 8,157,146 | B2 | 4/2012 | Edoga et al. |
| 8,231,639 | B2 | 7/2012 | Bolduc et al. |
| 8,685,044 | B2 | 4/2014 | Bolduc et al. |
| 8,690,897 | B2 | 4/2014 | Bolduc |
| 9,241,710 | B2 * | 1/2016 | Paz .................... A61B 17/0644 |
| 9,320,503 | B2 | 4/2016 | Bolduc |
| 9,320,589 | B2 | 4/2016 | Bolduc |
| 9,320,591 | B2 | 4/2016 | Bolduc |
| 9,808,250 | B2 | 11/2017 | Bolduc et al. |
| 9,848,869 | B2 | 12/2017 | Bolduc et al. |
| 9,867,611 | B2 | 1/2018 | Smith et al. |
| 9,968,353 | B2 | 5/2018 | Bolduc et al. |
| 9,974,671 | B2 | 5/2018 | Bolduc et al. |
| 10,194,905 | B2 | 2/2019 | Bolduc et al. |
| 10,299,791 | B2 | 5/2019 | Bolduc |
| 10,357,230 | B2 | 7/2019 | Bolduc |
| 10,595,867 | B2 | 3/2020 | Bolduc et al. |
| 11,103,341 | B2 | 8/2021 | Arbefeuille et al. |
| 11,896,509 | B2 | 2/2024 | Teichman et al. |
| 2003/0220683 | A1 | 11/2003 | Minasian et al. |
| 2005/0009673 | A1 | 1/2005 | Harris |
| 2005/0033398 | A1 | 2/2005 | Seguin |
| 2009/0048665 | A1 * | 2/2009 | Miron .................... A61B 17/11 623/1.36 |
| 2011/0106148 | A1 | 5/2011 | Ginn et al. |
| 2012/0130470 | A1 | 5/2012 | Agnew et al. |
| 2012/0172968 | A1 | 7/2012 | Chuter et al. |
| 2013/0023981 | A1 * | 1/2013 | Dierking ................ A61F 2/848 623/1.36 |
| 2013/0172983 | A1 | 7/2013 | Clerc et al. |
| 2015/0018933 | A1 * | 1/2015 | Yang ........................ A61F 2/07 623/1.14 |
| 2017/0056174 | A1 | 3/2017 | Tobis et al. |
| 2017/0333029 | A1 | 11/2017 | O'Hara et al. |
| 2018/0014956 | A1 | 1/2018 | Horgan et al. |
| 2018/0036111 | A1 | 2/2018 | Despalle De Béarn |
| 2018/0116798 | A1 | 5/2018 | Perszyk |
| 2018/0289476 | A1 | 10/2018 | Vyas et al. |
| 2019/0015633 | A1 | 1/2019 | Bednarek et al. |
| 2020/0086084 | A1 | 3/2020 | Sapir et al. |
| 2022/0331133 | A1 | 10/2022 | Teichman et al. |

FOREIGN PATENT DOCUMENTS

| | | |
|---|---|---|
| CN | 107530166 | 1/2018 |
| EP | 2008616 | 12/2008 |
| EP | 3167850 | 5/2017 |
| JP | 2005-525910 | 9/2005 |
| JP | 2009-528113 | 8/2009 |
| JP | 2009-233201 | 10/2009 |
| WO | WO 2019/239409 | 12/2019 |
| WO | WO-2022064492 A1 | 3/2022 |
| WO | WO-2023058023 A1 | 4/2023 |

OTHER PUBLICATIONS

Examination Report Under Sections 12 & 13 of the Patents Act, 1970 and the Patents Rules, 2003 Dated Aug. 17, 2022 From the Government of India, Intellectual Property India, Patents, Designs, Trade Marks, Geographical Indications, The Patent Office Re. Application No. 202027051804. (5 Pages).

International Search Report and the Written Opinion Dated Oct. 3, 2019 From the International Searching Authority Re. Application No. PCT/IL2019/050664. (10 Pages).

Notification of Office Action and Search Report Dated Oct. 28, 2023 From the State Intellectual Property Office of the People's Republic of China Re. Application No. 201980028381.5. (7 Pages).

Translation Dated Nov. 9, 2023 of Notification of Office Action Dated Oct. 28, 2023 From the State Intellectual Property Office of the People's Republic of China Re. Application No. 201980028381.5. (5 Pages).

Translation Dated Dec. 6, 2023 of Grounds of Reason of Rejection Dated Nov. 23, 2023 From the Korean Intellectual Property Office Re. Application No. 10-2020-7038128 (4 Pages).

Office Action Dated Aug. 16, 2023 From the Israel Patent Office Re. Application No. 279421. (4 Pages).

Notification of Office Action and Search Report Dated Mar. 1, 2023 From the State Intellectual Property Office of the People's Republic of China Re. Application No. 201980028381.5 (6 Pages).

Translation Dated Mar. 9, 2023 of Notice of Reason(s) for Rejection Dated Feb. 14, 2023 From the Japan Patent Office Re. Application No. 2020-568335. (9 pages).

Translation Dated Mar. 14, 2023 of Notification of Office Action and Search Report Dated Mar. 1, 2023 From the State Intellectual Property Office of the People's Republic of China Re. Application No. 201980028381.5 (3 Pages).

International Preliminary Report on Patentability Dated Dec. 24, 2020 From the International Bureau of WIPO Re. Application No. PCT/IL2019/050664. (8 Pages).

Notice of Reason(s) for Rejection Dated Feb. 14, 2023 From the Japan Patent Office Re. Application No. 2020-568335. (6 pages).

Grounds of Reason of Rejection Dated Nov. 23, 2023 From the Korean Intellectual Property Office Re. Application No. 10-2020-7038128 (5Pages).

Extended European Search Report and the European Search Opinion Dated Feb. 14, 2022 From the European Patent Office Re. Application No. 19819405.2. (8 pages).

Supplementary European Search Report and the European Search Opinion Dated Mar. 3, 2022 From the European Patent Office Re. Application No. 19819405.2. (1 page).

International Search Report and Written Opinion for International Application No. PCT/IL2021/051152, mailed Mar. 1, 2022, 12 Pages.

International Search Report and Written Opinion for International Application No. PCT/IL2022/051058, mailed Feb. 17, 2023, 8 Pages.

* cited by examiner

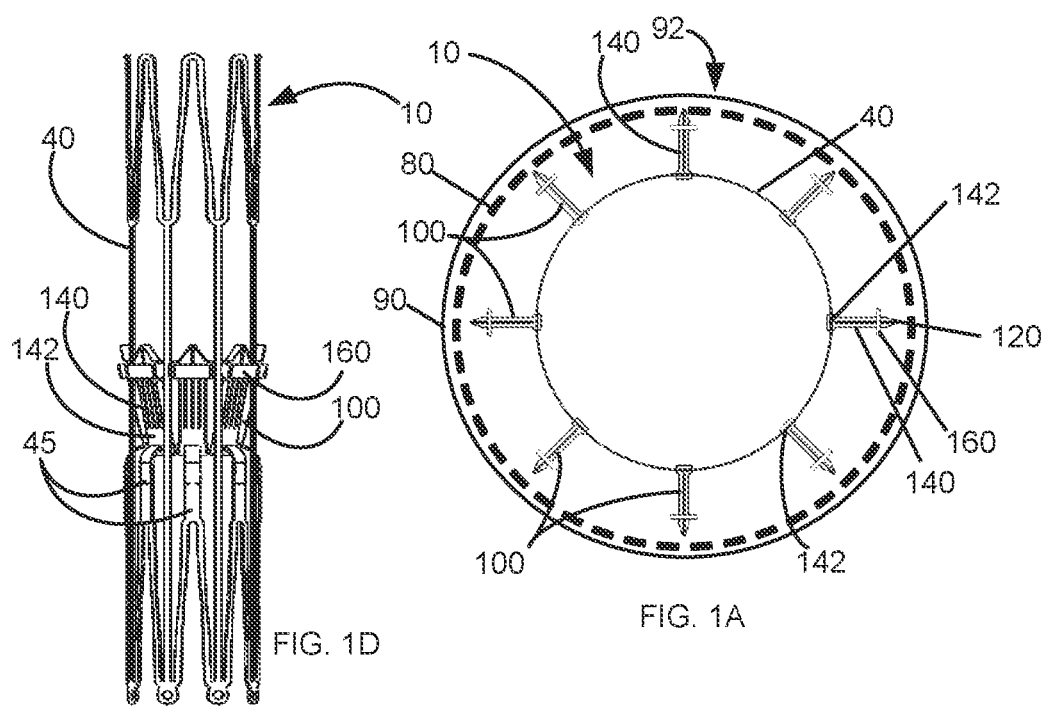
FIG. 1D
FIG. 1A
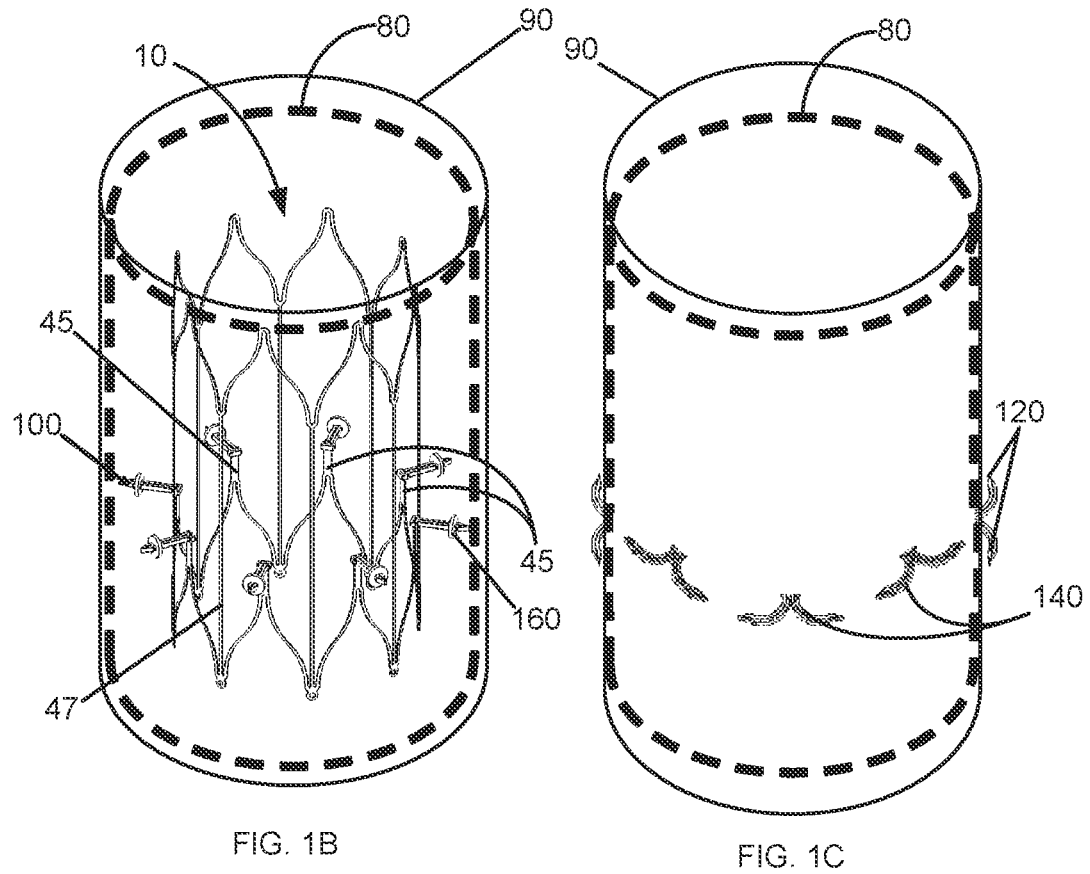
FIG. 1B
FIG. 1C

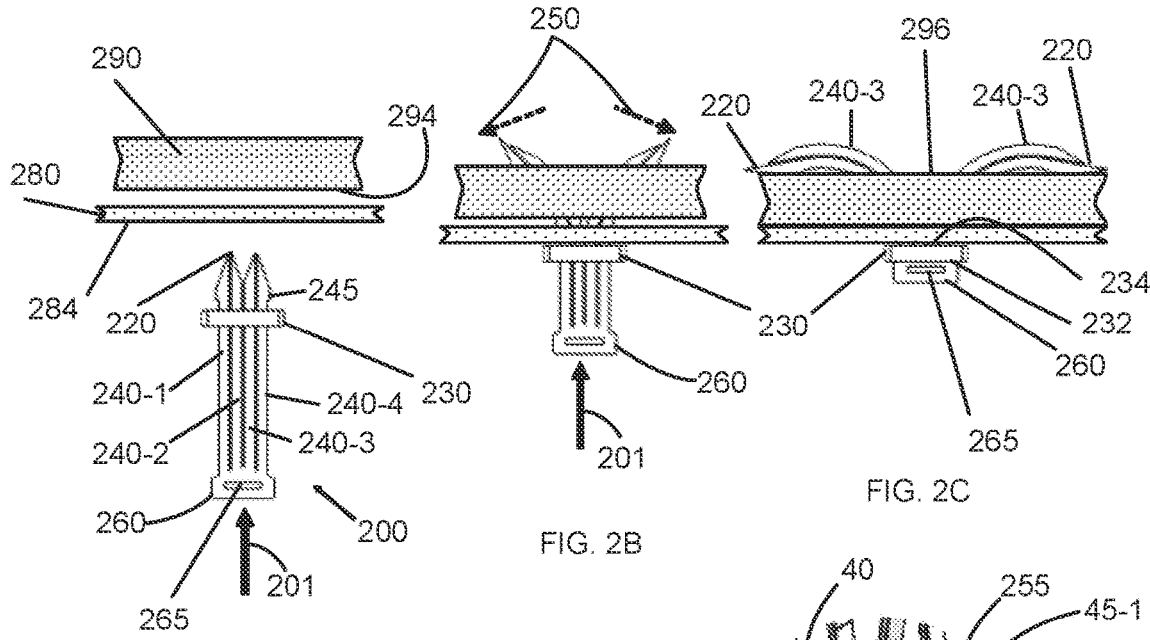
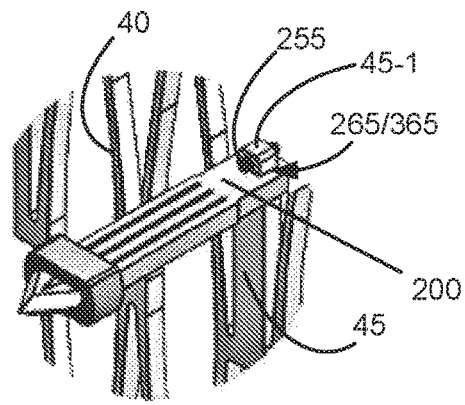
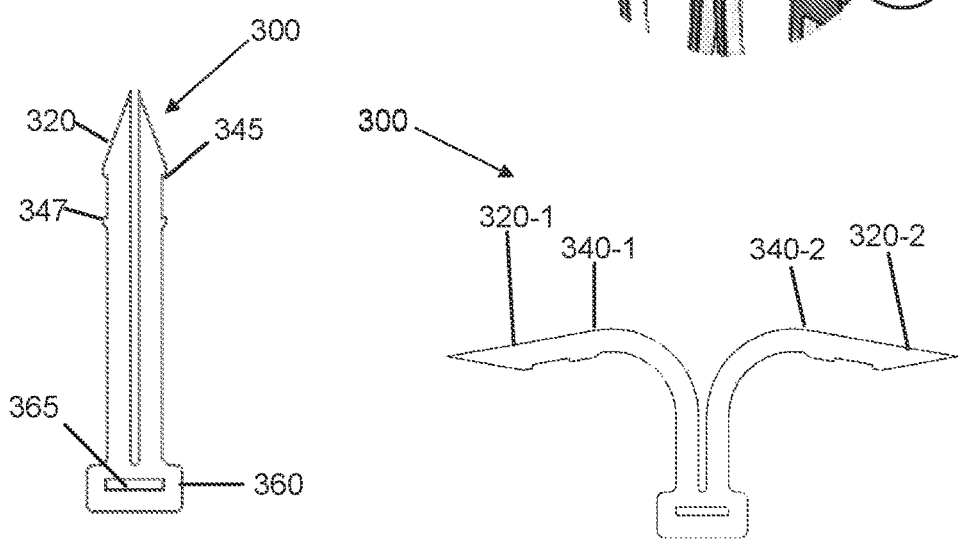

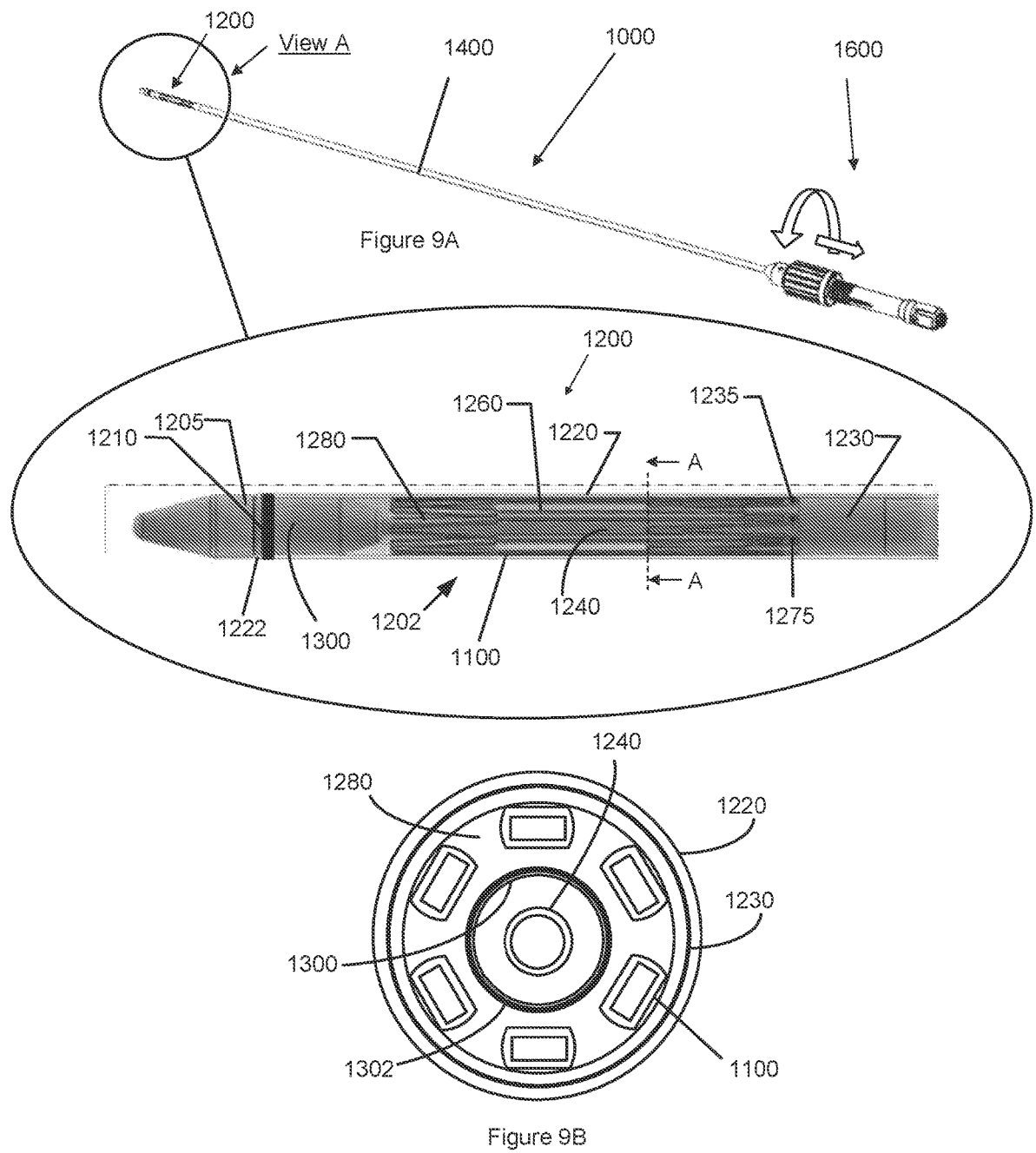

GRAFT SECURING SYSTEM, APPLICATOR AND METHOD

RELATED APPLICATIONS

This application is a US Continuation of PCT Patent Application No. PCT/IL2019/050664 having the international filing date of Jun. 12, 2019, which claims the benefit of priority under 35 USC § 119(e) of U.S. Provisional Patent Application No. 62/684,339, filed on Jun. 13, 2018.

PCT Patent Application No. PCT/IL2019/050664 is also related to U.S. patent application Ser. No. 12/224,601, filed on Sep. 2, 2008, entitled "FASTENING DEVICE".

The contents of the above applications are all incorporated by reference as if fully set forth herein in their entirety.

FIELD AND BACKGROUND OF THE INVENTION

The present invention, in some embodiments thereof, relates to systems and methods for repairing aneurysms and, more particularly, but not exclusively, to systems and methods for securing grafts to blood vessel walls.

An aneurysm is a bulging, weak spot in the aorta that may be at risk for rupturing. In some cases, the aneurysm is in the descending aorta that is in the abdomen.

Open repair that involves a large incision in the abdomen to expose the aorta and application of a graft to repair the aneurysm. Open repair remains the standard procedure for an abdominal aortic aneurysm repair.

Endovascular aneurysm repair (EVAR) is a minimally invasive option in which case the large abdominal incision is replaced by a small incision in the groin. Surgical instruments are driven through a catheter in an artery in the groin and threaded up to the aneurysm. At the aneurysm, a stent and a graft are deployed and positioned to support the aneurysm. An exemplary EVAR aneurysm repair method is disclosed in U.S. patent application Ser. No. 12/224,601.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

According to an aspect in accordance with some embodiments of the invention, there is provided a graft securing system, including: at least one expandable frame moveable from a collapsed state to an expanded state, and at least one anchor coupled to the frame via an elastic support strut, the anchor including: an anchor base, at least one deflectable prong protruding from the anchor base and having at least one penetration tip, and at least one restraining sleeve at least partially slideably moveable along the at least one prong, and in the collapsed state, the support strut is biased radially centrally bringing the at least one anchor to point generally axially, parallel to a longitudinal axis of the frame. In some embodiments, in the expanded state, the support strut moves from the biased radially centrally state to a free straightened state bringing the at least one anchor to point radially outwards.

According to some embodiments, the system includes a graft at least partially enveloping the frame. In some embodiments, movement of the frame from the collapsed state to the expanded state drives the anchor through the graft and into the tissue. In some embodiments, the anchor includes a plurality of prongs biased in an open configuration to be at least partially deflected away from each other. In some embodiments, in a fully open state, the prongs are deflected away from each other and apply force radially centrally securing the graft between the tissue and the frame. In some embodiments, the anchor includes at least two juxtaposed prongs and the sleeve-stop includes a resilient outwardly curved proximal portion of at least one of the prongs.

According to some embodiments, at least a portion of the sleeve-stop abuts the anchor base. In some embodiments, the sleeve-stop interferes with proximal movement of the restricting sleeve urged against the sleeve-stop at a first force at which the anchor partially penetrates the tissue via the graft. In some embodiments, at a second force, greater than the first force the restricting sleeve is configured to urge the resilient outwardly curved proximal portion of at least one of the prongs radially centrally in respect to the prongs and slide proximally over the sleeve-stop. In some embodiments, at the second force the anchor fully penetrates the tissue via the graft.

According to some embodiments, the anchor includes at least two juxtaposed prongs including a buckling prevention lock. In some embodiments, the buckling prevention lock includes at least one protrusion extending from a first prong and received within a recess in a juxtaposed second prong. In some embodiments, the sleeve is a penetrating sleeve. In some embodiments, the sleeve includes at least one sharp tapered penetration tip. In some embodiments, a tip of the anchor is ground along at least one distal edge of at least one prong and forms at least one penetrating blade. In some embodiments, the distal edge is pointed from its narrow aspect and flat from its wide aspect. In some embodiments, the distal edge is pointed from both its narrow aspect and its wide aspect. In some embodiments, the frame includes a partially expanded state at which configured to maintain longitudinal stability of the frame during axial movement along a vessel wall.

According to some embodiments, the at the partially expanded state the frame includes one of a bottle neck shape and an hourglass shape. In some embodiments, the system includes an anchor-to-frame mounting system. In some embodiments, the anchor-to-frame mounting system includes: at least one anchor including a cutout, an elastic support strut includes a matching end having a pinhole, and a locking pin, and in a mounted state, the anchor elastic support strut matching end is threaded inside the cutout and the locking pin is threaded through the pinhole. In some embodiments, the pin is welded to the anchor elastic support strut matching end by single point welding.

According to an aspect of some embodiments in accordance with the current invention there is provided an applicator for a graft securing system, including: a control handle, an applicator head including a container portion, and at least one lumen connecting the handle to the applicator head, the container sized to accommodate a graft securing system including: at least one expandable frame moveable from a collapsed state to an expanded state, and at least one anchor coupled to the frame via a flexible support strut, the anchor including: an anchor base, at least one deflectable prong protruding from the anchor base and having at least one penetration tip, and at least one restraining sleeve at least partially slideably moveable along the at least one prong, and in the collapsed state, the support strut is biased radially centrally bringing the at least one anchor to point generally axially, parallel to a longitudinal axis of the frame.

In some embodiments, the head includes at least one balloon. In some embodiments, the applicator includes a protective sleeve over the balloon. In some embodiments, the protective sleeve is made of silicone. In some embodiments, the balloon is axially moveable at least within the container. In some embodiments, the balloon and the frame are arranged concentrically. In some embodiments, the balloon is positioned distally to the frame. In some embodiments, the container includes at least one graft securing system frame holder and driver and at least one releasing sheath slidable over the graft securing frame holder and driver. In some embodiments, the frame holder and driver includes at least one frame holding pin disposed circumferentially at an external surface of the holder and driver.

In some embodiments, the frame includes at least one hole at least one end sized to receive the at least one holding pin. In some embodiments, the at least one releasing sheath is slidable distally towards the applicator tip over the frame and configured to lock the frame in place. In some embodiments, the at least one releasing sheath is slidable proximally away from the applicator tip releasing the frame.

According to an aspect of some embodiments of the current invention there is provided a method for deploying a graft securing system including: positioning a graft securing system applicator at a desired location, partially expanding a frame and partially driving one or more anchors into tissue via a graft, optionally verifying the deployment location and orientation of the frame in respect to the tissue and at least one of fully expanding the frame and fully driving the anchors into the tissue, and retracting the frame and repositioning the applicator. In some embodiments, the method comprises locking at least one end of the frame prior to positioning the graft securing system. In some embodiments, the method comprises partially expanding the frame while the at least one end is locked. In some embodiments, the method comprises locking the frame by sliding a releasing sheath distally over the frame. In some embodiments, the method comprises releasing the frame by retracting a releasing sheath proximally and exposing the frame.

According to an aspect of some embodiments in accordance with the current invention there is provided a method for deploying a graft securing system including: positioning a graft securing system applicator at a desired location, positioning a balloon within a distal portion of graft securing system frame, concurrently or consecutively partially exposing at least a portion of the graft securing system frame and allowing self-expansion of at least the distal portion, expanding the balloon from a deflated state to an expanded state and urging the partially expanded distal portion of the frame against a graft and the tissue, deflating the balloon, fully exposing and allowing self-expansion of the frame, while concurrently releasing and urging anchors of the graft securing system radially outwards to at least partially penetrate the graft and tissue, translating the balloon proximally and positioning the balloon fully within the frame, and fully expanding and urging the frame against the graft tissue thereby fully implanting the anchors in the tissue and securing the graft to the tissue.

According to an aspect of some embodiments in accordance with the current invention there is provided a graft securing kit including: at least one graft securing system, including: at least one expandable frame moveable from a collapsed state to an expanded state, and at least one anchor coupled to the frame via a flexible support strut, the anchor including: an anchor base, at least one deflectable prong protruding from the anchor base and having at least one penetration tip, and at least one restraining sleeve at least partially slideably moveable along the at least one prong, and in the collapsed state, the support strut is biased radially centrally bringing the at least one anchor to point generally axially, parallel to a longitudinal axis of the frame, and at least one applicator including: a control handle, an applicator head including a container portion, and at least one lumen connecting the handle to the applicator head, the container sized to accommodate at least the graft securing system.

In addition to the exemplary aspects and embodiments described above, further aspects and embodiments will become apparent by reference to the figures and by study of the following detailed description.

BRIEF DESCRIPTION OF THE SEVERAL VIEWS OF THE DRAWINGS

Exemplary embodiments are illustrated in referenced figures. Dimensions of components and features shown in the figures are generally chosen for convenience and clarity of presentation and are not necessarily shown to scale. The figures are listed below.

FIG. 1A is a top view simplified illustration of a graft securing system in accordance with some embodiments of the invention;

FIGS. 1B, 1C and 1D are perspective view and side view simplified illustrations of a graft securing system in accordance with some embodiments of the invention;

FIGS. 2A-2D are side view and perspective view simplified illustrations of an anchor of a graft securing system in accordance with some embodiments of the invention;

FIGS. 3A and 3B, are side view simplified illustrations of an anchor of a graft securing system in accordance with some embodiments of the invention;

FIGS. 9A and 9B are perspective view, side view and cross section view simplified illustrations of a delivery system for a graft securing system delivery device in accordance with some embodiments of the invention;

DESCRIPTION OF SPECIFIC EMBODIMENTS OF THE INVENTION

Figure 4A:
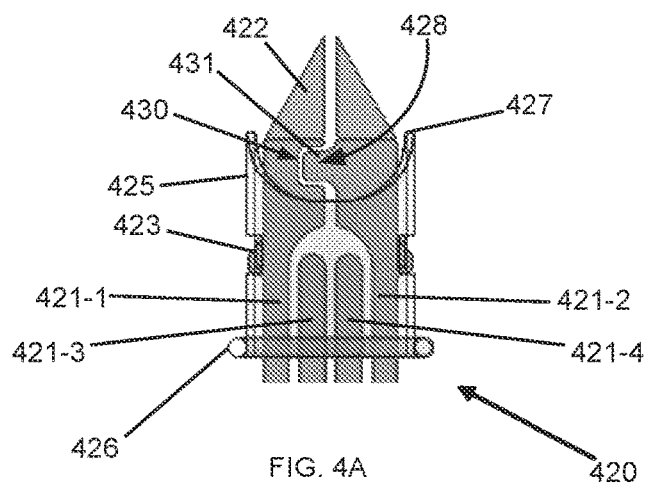
FIGS. 4A, 4B, 4C, 4D and 4E are plan view, partial cross-section view, side view and perspective view simplified illustrations of an anchor of a graft securing system in accordance with some embodiments of the invention.

According to an aspect of some embodiments of the invention there is provided a graft securing system, having a frame and a plurality of anchors mounted on the frame and configured to approximate and attach a graft to a blood vessel wall. In some embodiments, the blood vessel is the aorta. In some embodiments, the graft is a stent-graft. In some embodiments, the graft is sandwiched between the frame and the blood vessel wall. In some embodiments the frame comprises a ring form.

In accordance with some embodiments of the invention, the frame is expandable to an expanded state and collapsible to a retracted state. In some embodiments, in the expanded state, the frame urges the anchors that translate radially outwards and penetrate a wall of a tubular structure e.g., a blood vessel, from an internal surface (e.g., endothelial side) of the vessel facing the frame through the vessel wall. As is explained in detail elsewhere herein, once the anchors penetrate the vessel wall, they deform to engage an external surface of the vessel wall. In some embodiments, the anchors are urged through a graft prior to penetrating the wall of the vessel, so that the anchors penetrate the graft followed by the vessel wall and affix the graft to the blood vessel wall. In some embodiments, the frame applies a radially outwards force to the anchors.

According to an aspect of some embodiments of the invention there is provided a graft securing system, comprising a frame and a plurality of anchors mounted on the frame, and comprising one or more prongs protruding from a base of the anchor, and a restraining sleeve slidably mounted on and encircling the prongs, wherein the prongs comprise a distal (away from the frame and towards the tissue) penetration tip and one or more sleeve-stops e.g., restraining grooves, configured to temporarily prevent sliding of the restraining sleeve along the prongs and/or the penetration tip.

In some embodiments, the anchor penetration tip is wider than a prong portion just proximal (towards the frame and away from the anchor tip) to and adjacent to the penetration tip. In some embodiments, a sleeve-stop is formed on at least one prong and restricts at least a portion of the restraining sleeve from sliding distally over the penetration tip. In some embodiments, the sleeve length is shorter than the length of the prongs, so that the sleeve is slidable along the prongs between the sleeve-stop and the anchor base.

In some embodiments, sliding the restraining sleeve from the distal end of the anchor to the proximal end of the anchor brings the anchor from a restrained-closed state to an unrestrained-open state. In some embodiments, in the restrained configuration, the anchor prongs are juxtaposed in a closed state. In some embodiments, in the unrestrained configuration the anchor prongs are in an open state in which the prongs are at least partially deflected away from each other. In some embodiments, the prongs are resilient. In some embodiments, the prongs are made of a shape memory material. According to some embodiments of the invention, when the restraining sleeve is urged towards the base of the anchor, the restraining sleeve slides towards the base of the anchor over the prongs, thereby freeing the prongs to bend in any direction.

According to an aspect of some embodiments of the invention there is provided a graft securing system, comprising one or more ring-shaped frames, comprising a plurality of anchors protruding radially outward. In some embodiments, the ring-shaped frames are configured to penetrate tissue when urged against the tissue by radial expansion of the ring-shaped frames. In some embodiments, the system comprises two or more ring-shaped frames, and one or more latches configured to secure at least two rings to each other after being axially juxtaposed.

According to some embodiments of the invention, one or more of the rings form a stent-like frame configured to be secured to and support a blood vessel. According to some embodiments of the invention, the anchors of at least one of the rings comprise a penetration tip at the distal end and an anchor base at the proximal end, two or more prongs protruding distally from the anchor base and forming the penetration tip of the anchor at their distal end and a restraining sleeve, slidingly enclosing the anchor prongs and restricting the deflection of the prongs. In some embodiments, the restraining sleeve is slidable on and along the prongs between the anchor base and the penetration tip.

According to an aspect of some embodiments of the invention there is provided a graft securing system applicator comprising: one or more lumens coupled at a distal end to an applicator head. In some embodiments, the applicator comprises a container portion at a proximal end of the applicator lumen. In some embodiments, the graft securing system is disposed within the container portion prior to applying the securing system within a treatment site. In some embodiments, applicator container comprises one or more axially movable sheaths disposed over the at least a portion of the securing system. In some embodiments, a securing system holder is disposed at a proximal end of the head lumen.

According to some embodiments, the graft securing system is delivered by the applicator to a treatment site via a delivery catheter.

Graft Securing System

Reference is now made to FIGS. 1A to 1C, which are top view and perspective view simplified illustrations of a graft securing system in accordance with some embodiments of the invention. As shown in FIGS. 1A-1C, graft securing system 10 comprises: a frame 40 and a plurality of anchors 100. In some embodiments, anchors 100 comprise one or more prongs 140 connected at a base 142 and held in a restricted configuration by a restraining sleeve 160. In some embodiments, frame 40 is cylindrical or tubular.

In accordance with some embodiments of the invention, the anchors 100 secure a graft 80 to a blood vessel wall 90. In some embodiments, the frame 40 moves the anchors 100 radially outward (away from the frame 40), which, in turn penetrate the graft 80 and the wall of blood vessel 90. In some embodiments, the anchors 100 translate the radially outward force applied by frame 40 into a penetrating force and penetrate graft 80. Anchors 100 approximate and attach graft 80 to the blood vessel wall 90.

According to some embodiments, after penetrating the graft 80 and blood vessel wall 90, the anchors 100 assume an expanded state, in which prongs 140 of the anchors 100 deflect to lie against an outer surface 92 of blood vessel wall 90 and urge blood vessel wall radially centrally (towards the frame 40) against graft 80 and, optionally, frame 40.

A potential advantage in this configuration for approximating blood vessel wall 90 and graft 80 is in that in the fully expanded state, prongs 140 are deflected away from each other and apply force radially centrally securing the graft between the tissue and the frame 40 so that graft 80 and the vessel wall 90 are sandwiched between anchor 100 prongs 102 and base 142 and frame 40 struts.

Blood vessel wall 90 and graft 80 are secured to each other at the blood vessel wall site of penetration by anchor 100 with no necessary physical contact between frame 40 and the graft. In some embodiments, the graft 80 is a stent-graft.

In the exemplary embodiment depicted in FIGS. 1A-1C anchors 100 are mounted on frame 40 via one or more anchor support struts 45. In some embodiments and as shown in FIGS. 1A-1C, anchors 100 are mounted on anchor support struts 45 at an angle (e.g., 90 degrees) in respect to a longitudinal axis of frame 40 pointing radially outward. In some embodiments and as explained elsewhere herein, frame 40 is radially expandable and collapsible.

As shown in FIGS. 1A-1D, in accordance with some embodiments of the invention, the frame 40 is expandable and collapsible. In some embodiments, the frame 40 is a radially expandable securing ring. In some embodiments as shown in FIGS. 1B, 1C and 1D, the frame 40 is stent-like however, frame 40 may comprise any suitable collapsible/expandable structure. In some embodiments, frame 40 is expandable from a collapsed state (FIG. 1D) to an expanded state (FIGS. 1B and 1C). In some embodiments, the system comprises a stent graft within or outside frame 40. In some embodiments, the stent graft lies between frame 40 and the vessel wall.

In some embodiments, and as showed in FIG. 1A, in the collapsed state, frame 40 e.g., when within releasing sheath 1230 as explained in greater detail herein, anchor support struts 45 are elastically biased radially centrally bringing anchors 100 to point generally axially, parallel to longitudinal axis of frame 40.

In some embodiments, in the expanded state shown for example in FIG. 1B, anchor support struts 45 move by an elastic force from the biased radially centrally state to a free straight state in which support struts 45 are straightened and are realigned with the longitudinal axis of frame 40, bringing anchors 100 to point radially outward. In some embodiments, at the expanded state anchors 100 are angled generally perpendicularly to longitudinal axis of frame 40.

As shown in FIG. 1A-1C, anchor 100 comprises an anchor base 142 configured for mounting the anchor 100 on the frame 40 and two or more adjacent prongs 140 protruding from the anchor base 142 and forming a penetration tip 120. Anchor 100 comprises a restraining sleeve 160 mounted on prongs 140. In some embodiments, restraining sleeve 160 encircles prongs 140. In some embodiments, restraining sleeve 160 limits the prongs 140 from deflecting in opposing directions.

Turning to FIGS. 2A to 2D, which are side view and perspective view simplified illustrations of implementation of an anchor 200 in accordance with some embodiments of the invention. For the purpose of simplifying the explanation the anchors shown in FIGS. 2A-2C, 3A-3B, 4A-4C and 5, anchors are shown detached from the frame 40 and the anchor support strut 45.

As shown in FIG. 2A, a graft 280 and the blood vessel wall 290 are disposed adjacent to each other. As shown in FIGS. 2A and 2B, anchor 200 is urged against graft 280 and blood vessel wall 290 by a force (indicated by arrow 201) applied to anchor base 260 in a radially outward direction.

In operation, force 201 is generated by expansion of frame 40. The penetration tips 220 of anchor 200 penetrate the graft 280 from an inner surface 284 of the graft 280, through graft 280 and into an inner (e.g., endothelial) surface 294 of the blood vessel wall 290, to engage an opposing outer surface 296 thereof.

As shown in FIG. 2A, anchor 200 comprises one or more prongs 240 and a restraining sleeve 230. In some embodiments, the length of restraining sleeve 230 is shorter than the length of prongs 240, thereby the restraining sleeve 230 is slidable over and along the prongs 240 between the penetration tip 220 and base 260. In some embodiments, the restraining sleeve 230 is blocked from sliding over the distal ends of prongs 240-1 and 240-4 by a restraining sleeve-stop 245 formed by the tips 220 of the prongs 240. In some embodiments, the base 260 of the anchor 200 is wider than the internal cross section of the restraining sleeve 230, thereby, sleeve 230 is limited from sliding proximally over the base 260 of the anchor 200. In some embodiments, the restraining sleeve-stop 245 is shaped as a rib protruding laterally outwards from prongs 240 and extend beyond an internal cross section of the restraining sleeve 230. As shown in FIGS. 2A to 2C, the prongs 240 are resilient and are made of a shape memory material e.g. Nitinol. The prongs 240 are pre-shaped to assume the pre-shaped unrestrained configuration in which the anchor prongs 240 are in an open state and the prongs 240 are deflected away from each other as indicated by broken-line arrows 250.

FIG. 2A depicts an exemplary embodiment in which anchor 200 is at a maximally restrained state, in which the anchor prongs 240-1 to 240-4 are juxtaposed throughout their length. FIG. 2C is an exemplified embodiment in which anchor 200 is at a maximally unrestrained state, and FIG. 2B is an exemplary embodiment in which anchor 200 is at a partially restrained state (or a partially unrestrained state). Anchor 200 is configured to assume a maximally restrained state (FIG. 2A) when restraining sleeve 230 engages restraining sleeve-stop 245 and pre-shaped to assume a maximally unrestrained state (FIG. 2C) when restraining sleeve 230 engages anchor base 260, is distant of the restraining sleeve-stop 245 and frees prongs 102 to bend into their pre-shaped open (unrestrained) state. In some embodiments as shown in FIG. 2B, the penetration tip 220 of any one of the prongs 240-1 to 240-4 is deflected laterally at a partially restrained state.

In some embodiments, and as shown in FIGS. 2A-2C, anchor 200 comprises four prongs 240 (240-1 to 240-4). Two prongs are internal prongs 240-2/240-3, disposed between two prongs 240-1/240-3 and 240-2/240-4 respectively). In some embodiments, two of the prongs are external prongs 240-1/240-4, each positioned next to an internal prong 240-2/240-3 respectively so that to form two pairs of prongs 240-1/240-2 and 240-3/240-4. In some embodiments, the two pairs of prongs 240-1/240-2 and 240-3/240-4 deflect away from each other when assuming an unrestrained state. In some embodiments, the internal prongs 240-2 and 240-3 are slidable along the adjacent external prongs 240-1 and 240-4 respectively when deflecting outwards towards an unrestrained state. In some embodiments, the internal prongs 240-2 and 240-3 apply deflecting force on the adjacent external prongs 240-1 and 240-4 respectively when deflecting to an open-unrestrained state.

As shown in FIGS. 2B and 2C, as restraining sleeve 260 slides towards the anchor base 230, the pair of the external prongs 240-1/240-4 and the internal prongs 240-2/240-3 deflect in opposite directions into the unrestrained state distancing penetration tips 220 from each other. In some embodiments, the internal prongs 240-2/240-3 and external prongs 240-1/240-4 apply an outwards oriented force vector to each side of the anchor 200. In the exemplary embodiment shown in FIGS. 2A-2C, the tip of the anchor 200 comprises a dual tip 220 of the two pairs of the internal prongs 240-2/240-3 and external prongs 240-1/240-4. In some embodiments, the force 201 applied on the anchor 200 by expanding the frame 40, is translated into a mechanical change in anchor 100 configuration allowing prongs 240 to bend in opposite directions and bring penetrating tips 220 to urge against external surface 296 of the blood vessel wall 290, opposite to the penetration direction thereby affixing the blood vessel wall 290 to graft 280.

In some embodiments the anchor 200 is in a fully expanded state and the graft 280 is sandwiched between the anchor 200 base 260 and the blood vessel wall 290 when restraining sleeve 230 is moved towards base 260. In some embodiments, sleeve 230 is moved to fully abut base 260 as shown in FIG. 2C.

In some embodiments as shown in FIGS. 1A and 2A-2C, a force applied on the restraining sleeve 160/230 initiates the sliding of the restraining sleeve 160/230 towards the anchor tip 120/220 (distally) or towards the anchor base 142/260 (proximally). In the exemplary embodiment depicted in FIGS. 2A-2C, blood vessel wall 290 and/or graft 280 resist penetration of restraining sleeve 160/230 creating a reactive force opposite to force 201. In some embodiments, the restraining sleeve 160/230 comprises an anchor base-facing flat surface 232 of restraining sleeve 160/230. In some embodiments, the restraining sleeve 160/230 comprises an anchor tip-facing flat surface 234. In some embodiments, the restraining sleeve 160/230 is urged in a proximal direction by a force applied on a base-facing surface 232 or a tip-facing flat surface 234 of the restraining sleeve 160/230. In some embodiments, as shown in FIGS. 2A-2C, restraining sleeve 230 is flat and short in length and is configured to remain inside the blood vessel and urged against the graft 280 while the prongs 240 penetrate the graft 280 and the blood vessel wall 290. In some embodiments, the sleeve 230 does not engage the inside (endothelial) surface of the blood vessel wall 290.

In some embodiments, and as shown in FIG. 2D, which is a perspective view of anchor 100-to-frame 40 mounting system. In FIG. 2D, anchor 100 is mounted on frame 40 being in an expanded state similar to that shown in FIG. 1B. In some embodiments, the anchor base 260 comprises a cutout 265, which is used to attach the anchor 200 onto an anchor support strut 45 of the frame 40 (e.g. a stent-like frame 40), by fitting the cutout 265 onto a matching end 45-1 of anchor support strut 45. In some embodiments, a locking pin 255 is driven via a pinhole in matching end 45-1 locking anchor 200 to the matching end 45-1 of anchor support strut 45. Since matching end 45-1 and cutout 265/365 as well as locking pin 255 share the stress involved with implementation of system 100, only movement of locking pin 255 within the pinhole needs to be secured. In some embodiments, pin 255 is glued, welded, bonded or attached in any other suitable technique to support strut 45. In some embodiments, the anchor 200 is locked to the frame 40 after being fitted on the frame 40. In some embodiments, the anchor 200 is integrally formed on the frame 40 by laser cutting and thermoforming manufacturing process.

A potential advantage in the locking mechanism of anchor 200 to support strut 45-1 attachment is in that the point of flexion or bending of support strut 45 is proximal and relatively distant from the attachment and thus and a zone surrounding locking pin 255 encounter minimal stress, at least than the stress encountered by support strut 45, while the anchor is forcibly aligned by the frame 40 and is not affected by bending elastic forces applied to support strut 45 reducing chances of weakening, breakage or detachment of anchor 100 from support strut 45.

A potential advantage in the locking mechanism of anchor 200 to support strut 45-1 is in that welded Nitinol is very sensitive to stress (e.g., stress resulting from bending). The described attachment-by-locking pin 255 solution includes single point welding to secure the locking pin 255.

Figure 4B:
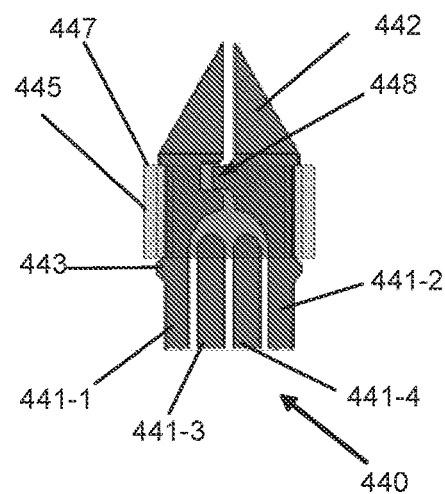
Figure 4C:
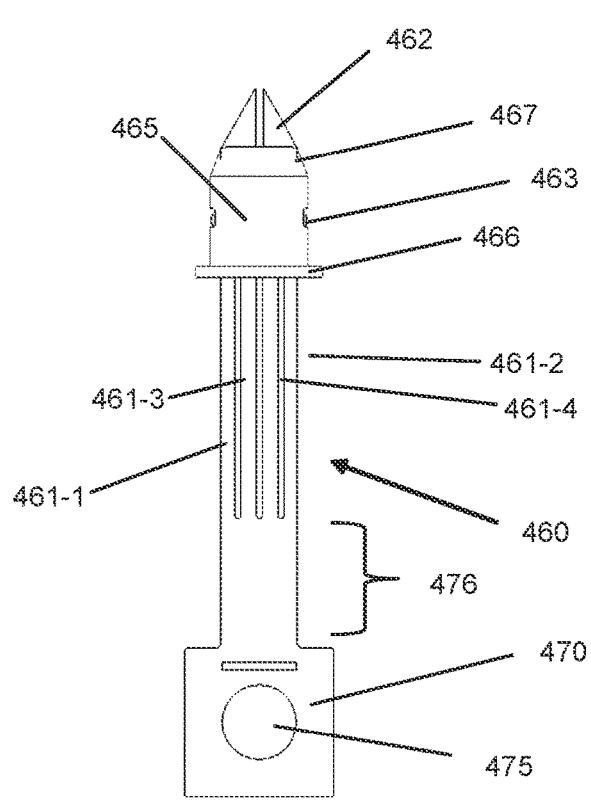
Figure 4D:
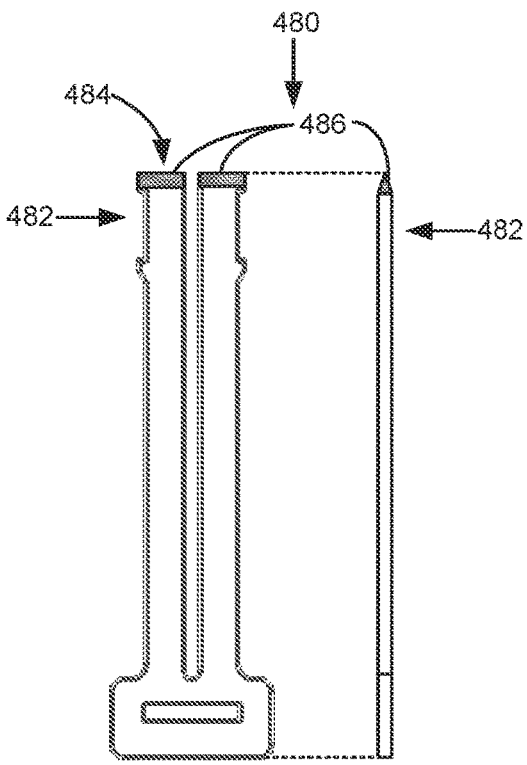
Figure 4E:
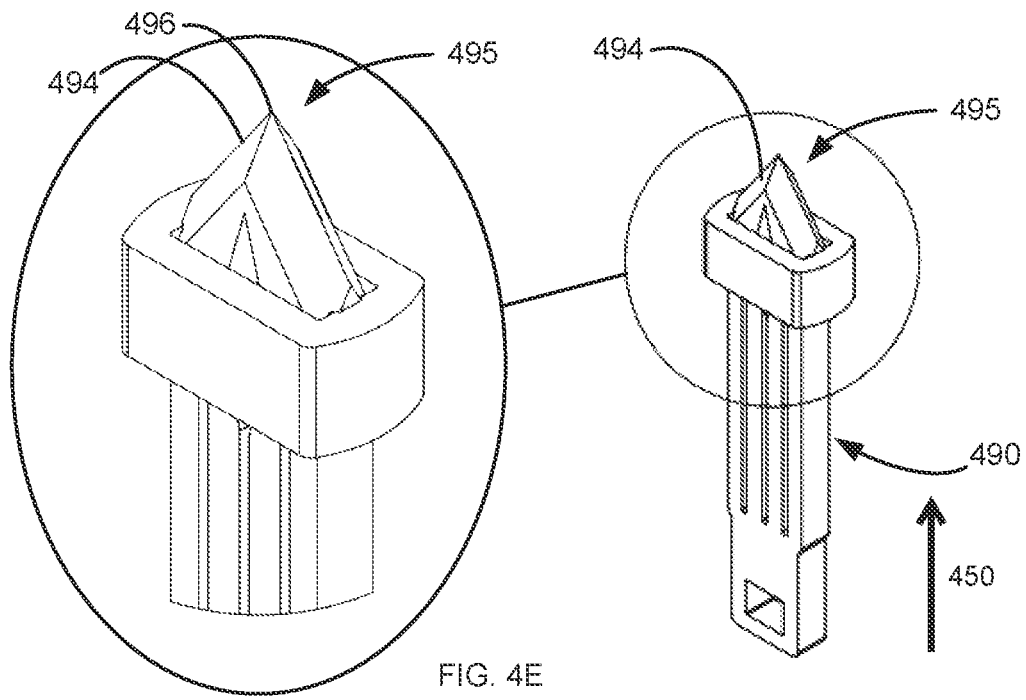

A potential advantage in the locking mechanism of anchor 200 to support strut 45-1 is in that a restraining sleeve can be threaded onto the anchor prongs in a distal direction from the base of the anchor, which is relatively narrow, towards the tip of the anchor, which is relatively wider, as indicated in FIG. 4E by arrow 450.

According to some embodiments of the invention as shown in FIGS. 2A-2C, the anchor 200 comprises an even number of prongs (four) 240 (240-1 to 240-4). In the exemplified embodiment of FIGS. 2A-2C two prongs 240-2/240-3 are internal prongs, disposed between two other prongs 240-1/240-3 and 240-2/240-4 respectively. Two of the prongs 240-1/240-4 are external prongs, each positioned next to an internal prong 240-2/240-3 respectively so that to form two pairs of prongs 240-1/240-2 and 240-3/240-4. In some embodiments, the anchor comprises an odd number of prongs. In some embodiments, the anchor comprises an odd number of internal prongs.

Referring now to FIGS. 3A and 3B, which are side view and perspective view simplified illustrations of an anchor 300 (excluding its restraining sleeve), in accordance with some embodiments of the invention. As shown in FIGS. 3A and 3B, in some embodiments, the anchor 300 comprises a pair of external prongs 340-1/340-2 and is free of internal prongs.

The anchor 300 shown in FIG. 3A in a maximally restrained position and FIG. 3B in maximally unrestrained position, comprise two prongs 340-1/340-2. The tip 320 of the anchor 300 is formed by two tip halves 320-1/320-2— one half on each prong so that juxtaposed prongs 340-1/340-2 bring tip halves 320-1/320-2 into juxtaposition to form a single complete tip 320. A potential advantage of this configuration is in that a force applied on the anchor 300 by a frame (not shown) results in juxtaposed prongs tip halves 320-1/320-2 to act as a single penetrating tip 320 in a closed state (FIG. 3A) while maintaining a lower material (e.g., Nitinol) volume and a low-profile in an open deployed state (FIG. 3B).

A potential advantage of this configuration is in that a single tip or a single tip comprising two halves of a tip has a smaller surface area in respect to a double-tipped anchor as shown in FIGS. 2A-2D and reduced resistance when penetrating graft 280 and blood vessel wall 290.

In the exemplary embodiment depicted in FIGS. 3A and 3B the anchor base 360 comprises a rectangular cut 365, which is used to attach the anchor 300 onto anchor support strut 45 of a frame 40, e.g. a stent or an expandable ring (not shown). As shown in FIGS. 3A and 3B, the restraining sleeve (not shown) is blocked from sliding over the anchor penetration tip 320 by a protruding restraining sleeve-stop 345 formed at the distal ends of prongs 340-1/2. In addition, the sliding of the restraining sleeve (not shown) towards base 360 is temporarily limited by a second protruding restraining sleeve-stop 347 formed between protruding restraining sleeve-stop 345 and the anchor base 360.

Reference is now made to FIGS. 4A to 4E which are plan, partial cross-section, side and perspective view simplified illustrations of penetration portions anchors, in accordance with some embodiments of the invention. The embodiments of the restraining sleeves depicted in FIGS. 4A to 4C can be combined mutatis mutandis with any one of the anchors shown in FIGS. 2A-3B.

In some embodiments (e.g. FIG. 4B), the restraining sleeve 425 is absent a tapered tip. In some embodiments, and as shown in FIG. 4A, restraining sleeve 425 of anchor 420 is a tissue penetrating restraining sleeve comprising one or more distal tapered penetration tips 427 configured to penetrate a graft and/or tissue. In some embodiments, penetration tips 427 comprise one or more sharp edges. A potential advantage in tapered penetrating tips is in that tapered tips reduce the level of resistance necessary for driving anchor 100 through the graft and/or vessel wall.

Additionally, and as shown in the exemplary embodiment depicted in FIG. 4A, restraining sleeve 425 is an in-tissue dwelling restraining sleeve and comprises a base-facing flange 426 that protrudes radially outwards from an external surface of sleeve 425. During implementation, tissue penetrating restraining sleeve 425 penetrates graft 280 and blood vessel wall 290 up to a point at which flange 426 abuts an internal surface of graft 280 and stops further penetration of tissue penetrating restraining sleeve 425 into the tissue. Continued application of force on base 260 by frame 40 brings anchor 420 prongs 421 to slide axially outwards in respect to tissue penetrating restraining sleeve 425 freeing prongs 421 to bend in opposite directions and bring penetrating tips 220 to urge against external surface 296 of the blood vessel wall 290, opposite to the penetration direction thereby affixing the blood vessel wall 290 to graft 280.

In some embodiments and as shown in the exemplary embodiment depicted in FIG. 4B, restraining sleeve 445 is an intra-lumen dwelling restraining sleeve. Intra-lumen dwelling restraining sleeve 445 is devoid penetrating tips and comprises a blunt distal (tip-facing) surface 447. During implementation, intra-lumen dwelling restraining sleeve 445 abuts an internal surface of graft 280 stopping intra-lumen dwelling restraining sleeve 445 from penetrating graft 280 or into the tissue. Continued application of force on base 260 by frame 40 brings anchor 440 prongs 421 to slide axially outwards in respect to intra-lumen dwelling restraining sleeve 445 freeing prongs 421 to bend in opposite directions and bring penetrating tips 220 to urge against external surface 296 of the blood vessel wall 290, opposite to the penetration direction thereby affixing the blood vessel wall 290 to graft 280.

As shown in FIGS. 4A and 4C, in some embodiments, restraining sleeve 425/465 comprises a base-facing flange 426/466. As shown in FIGS. 4A and 4B, in some embodiments, internal prongs 421-3/4 and 441-3/4 are shorter than the external prongs 421-1/2/441-1/2 and comprise blunt tips. In some embodiments, the anchor 420 comprises internal prongs 421-3/4 having blunt tips.

As shown in FIGS. 4A and 4B, in some embodiments, anchor 420/440 comprises a buckling prevention lock 428/448 at tip 422/442 configured to prevent anchor buckling during penetration into a graft and/or a tissue. In some embodiments, buckling lock 428 is formed by a protrusion (e.g., tongue-shaped) 430 protruding from a first prong 421-2 towards a juxtaposed second prong 421-1 and a recess 431 in the second prong 421-1 facing the protrusion 430 so that in a juxtaposed configuration of the first 421-1 and second 421-2 prongs, protrusion 430 is accommodated by recess 431 forming the buckling lock 428. In operation, when anchor 420 is urged by a frame (not shown) against and into a graft and a blood vessel wall (not shown). Buckling causes shear forces between layers, expressed as longitudinal movement between adjacent prongs. Lock 428 is configured to stop relative movement between the prongs 421-1/421-2 (e.g., relative axial movement of each prong in respect to the juxtaposed prong) and thus prevents the buckling of anchor 420 during penetration a graft and/or a blood vessel wall.

As shown in FIGS. 4A to 4C, in some embodiments, restraining sleeve-stop 423/443/463 is shaped as a rib protruding outward from a surface of the prong 421/441/461 and forming a ridge wider than that of an internal width of the restraining sleeve 425/445/465. In some embodiments, as shown in FIG. 4A, the external width of the prongs 421-1 to 421-4 between the protrusions 423 is equal or smaller than the external width of the restraining sleeve 425, thereby rib 423 does not protrude externally to the restraining sleeve 425. In some embodiments (FIGS. 4A to 4C) tips 422/442/462 protrude in an opposite direction to the restraining sleeve-stop 423/443/463.

According to some embodiments of the invention, a cross section of one or more prongs has a rectangular, flat, circular, triangular or any other suitable geometry. In some embodiments, the cross section of any one of the prongs varies along its length. In some embodiments, the cross section of the restraining sleeve is either one or a combination of: rectangular, flat, and circular.

In some embodiments, and as shown in the exemplary embodiments depicted, for example, in FIGS. 4A, 4B and 4C, a tip 422, 442 and 462 respectively of anchors 420, 440 and 460 respectively is cut (e.g., by laser) to form pointed (e.g., triangular) geometry. In some embodiments, during manufacturing distal edges 427/467 of restraining sleeve 425/465 are optionally ground to shape.

In some embodiments, and as shown in the exemplary embodiment depicted in FIG. 4D, a tip 482 of anchor 480 is ground along a distal edge 484 of the anchor to form a penetrating blade 486. In some embodiments, distal edge 484 is pointed from its narrow aspect and flat from its wide aspect. The blade-edge of the anchor tip depicted in FIG. 4D improved the penetrability of the anchor through the graft and the tissue.

In some embodiments, and as shown in the exemplary embodiment depicted in FIG. 4E, a tip 495 of anchor 490 is ground along both sides of a distal edge 494 of the anchor to form a pointed penetrating blade 496. In some embodiments, distal edge 494 is pointed from both its narrow aspect as well as from its wide aspect. The pointed blade-edge of the anchor tip depicted in FIG. 4E adds additional cutting edges than the single cutting blade edge of FIG. 4D adding additional penetrability of the anchor through the graft and the tissue. The selection between anchors 480 and 490 depends on the type of tissue and/or graft material the anchor is expected to penetrate.

Figure 5:
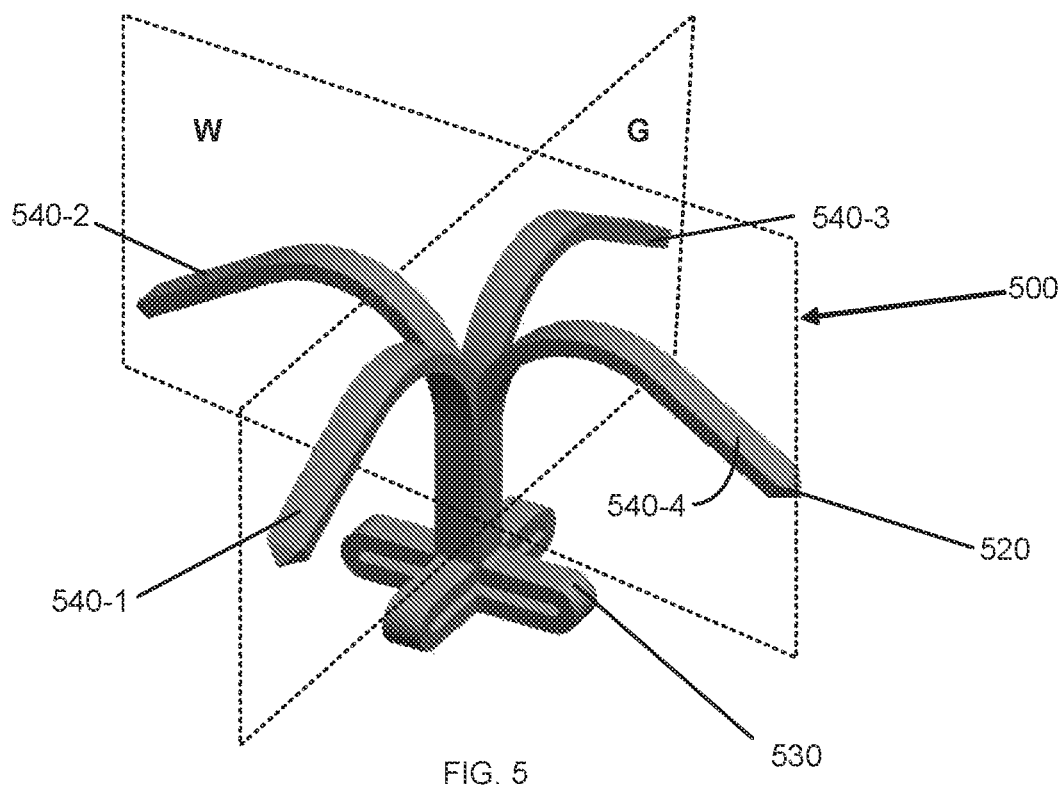
FIG. 5 is a perspective view simplified illustration of an anchor of a graft securing system in accordance with some embodiments of the invention.

Turning to FIG. 5 which is a perspective view simplified illustration of a 3D-anchoring anchor (excluding a restraining sleeve), in accordance with some embodiments of the invention. The anchor 500 shown in FIG. 5 comprises three or more prongs 540-1, 540-2, 540-3 and 540-4. In the exemplary embodiment depicted in FIG. 5, anchor 500 comprises two pairs of prongs 540 each pair comprising two diametrically opposed prongs 540 (e.g., 540-1/540-3 and 540-2/540-4) the prongs of each pair configured to bend in opposite directions along a common plane (e.g., plane G and Plane W respectively). In some embodiments, the planes G and W are angled in respect to each other. In some embodiments, the planes G and W are perpendicular in respect to each other.

A potential advantage of anchor 500 is in that it provides at least three points of pressure on an external surface of the blood vessel. A potential advantage of anchor 500 is in that it prevents rising or curving of the wall 290 of the blood vessel along sides of prongs 540, preventing partial detachment of blood vessel wall 290 from graft 280. In some embodiments, anchor 500 is made of flat/round NiTi wire or cut and shaped out of NiTi tube.

In some embodiments, an anchor such as anchor 500 is manufactured by cutting the anchor from sheet metal and forming the final anchor by bending the cut piece. In some embodiments, an anchor such as anchor 500 is manufactured by cutting the anchor from a tube (e.g., by laser) and forming the final anchor form with thermal treatment.

The prong 540-1 to 540-4 are oriented on the base so each prong is disposed between two other prongs (e.g. 540-1 is disposed between 540-2 and 540-3). In some embodiments, a restraining sleeve-stop is formed at the prongs.

Figure 6A:
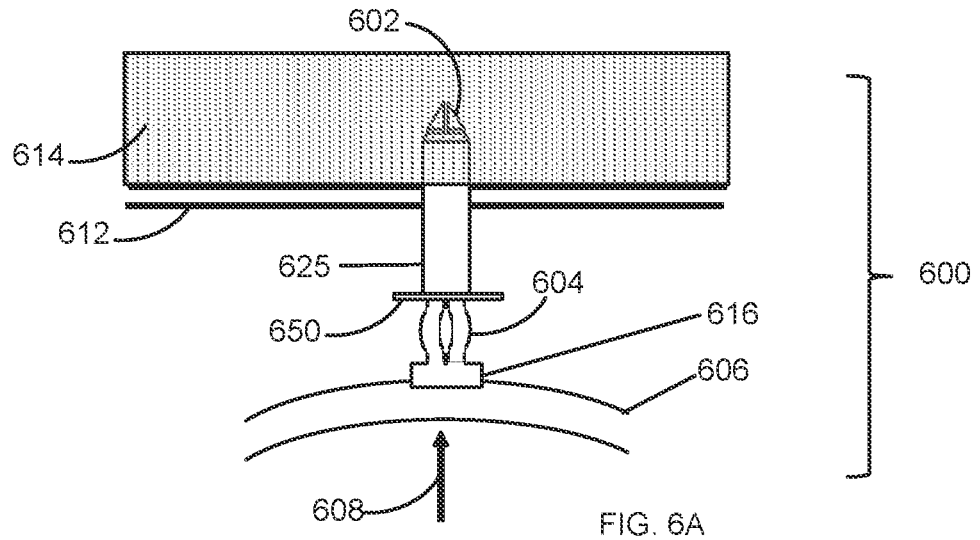
FIGS. 6A, 6B and 6C are side view simplified illustrations of implementation of a graft securing system in accordance with some embodiments of the invention.
Figure 6B:
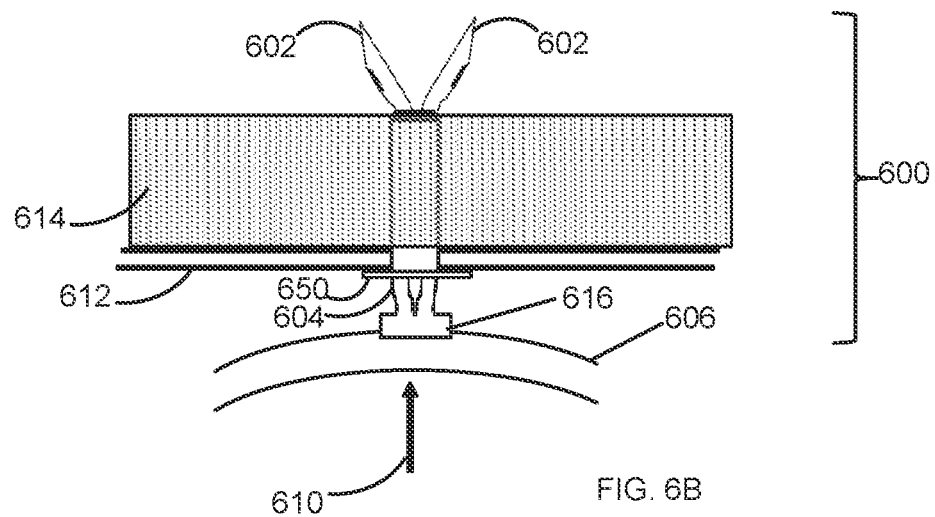
Figure 6C:
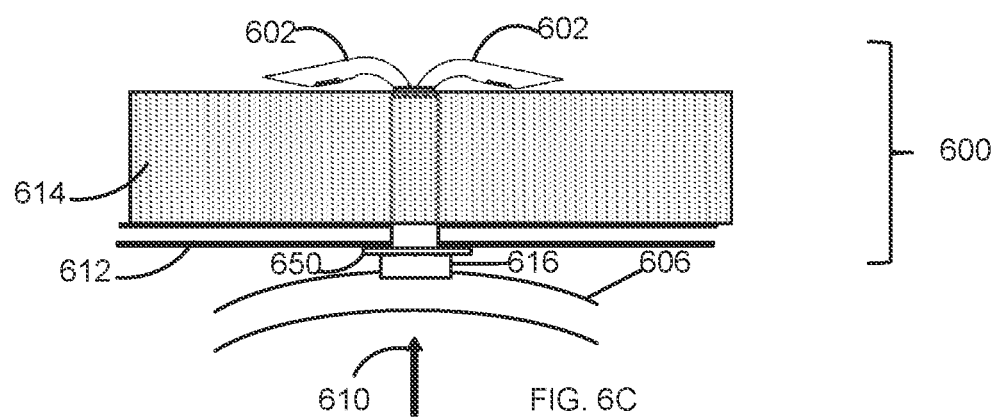

Reference is now made to FIGS. 6A, 6B, and 6C, which are side view simplified illustrations of implementation of a securing system 100 anchor 600 in accordance with some embodiments of the invention. In the exemplary embodiment of FIGS. 6A-6C, anchor 600 is double pronged, at least one prong 602 comprising a resilient outwardly curved proximal portion 604. In some embodiments, resilient outwardly curved proximal portion 604 are adjacent or abutting anchor 600 base 616. In some embodiments, resilient outwardly curved proximal portion 604 is resilient in a lateral direction (radially centrally and outwards) and is configured to move centrally and optionally axially (increasing the length of prongs 602) when urged radially inwards. In some embodiments, restraining sleeve 625 has cylinder geometry and comprises a flange 650 attached to a proximal (towards the frame 606) end of sleeve 625.

In some embodiments, anchor 600 is deployed into a blood vessel wall in a two-stepped process. At a first step, and as depicted in FIG. 6A, a low first force, represented by a thin arrow 608 is applied to frame 606 driving anchor 600 into tissue. The applied low force is sufficient to drive anchor 600 into the tissue but insufficient to force restraining sleeve 625 over resilient outwardly curved proximal portions 604.

As shown in FIG. 6B, a second force, higher than the first low force, represented by a thick arrow 610 is sufficient to urging flange 650 against a graft 612 and blood vessel endothelium 614, force restraining sleeve 625 to move in a proximal direction over resilient outwardly curved proximal portions 604 urging them in a radially inward direction. Proximal movement of restraining sleeve 625 further drives anchor 600 into tissue and frees at least a portion of anchor 600 prongs 602 to bend away from each other.

The exemplary embodiment shown in FIG. 6C shows the final deployment stage in which anchor 600 is fully deployed, restraining sleeve 625 abuts base 616 and prongs 602 are fully free and bent against an outside surface of the blood vessel wall securing graft 612 to the blood vessel wall.

Ring-Shaped Anchoring Securing Systems

Figure 7A:
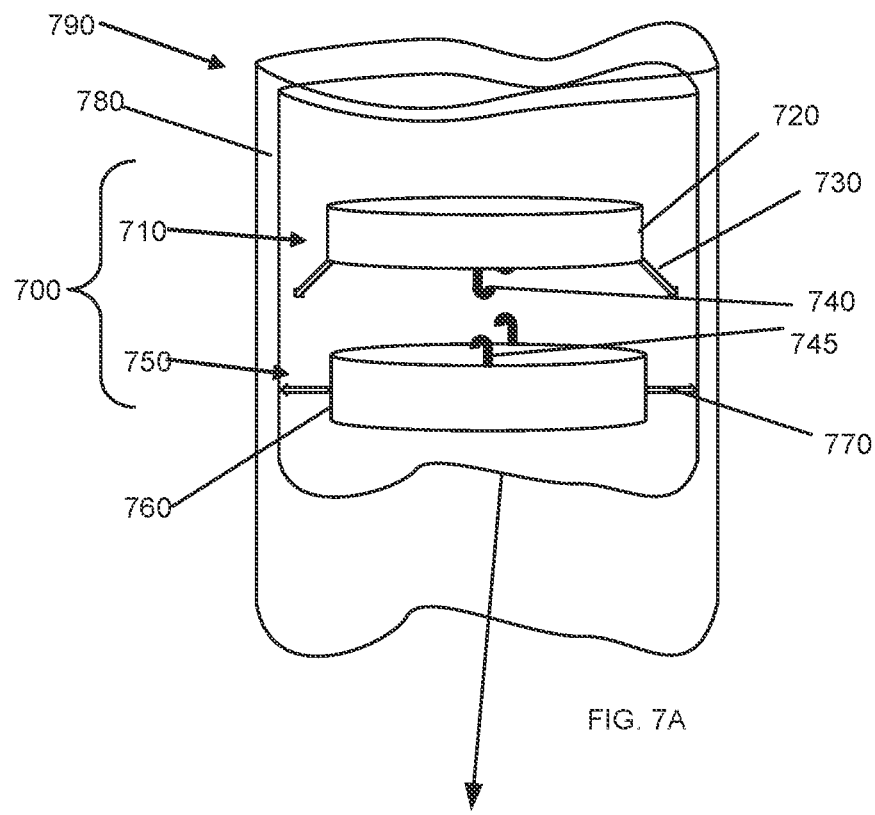
FIGS. 7A and 7B are perspective view simplified illustrations of a graft securing system in accordance with some embodiments of the invention.
Figure 7B:
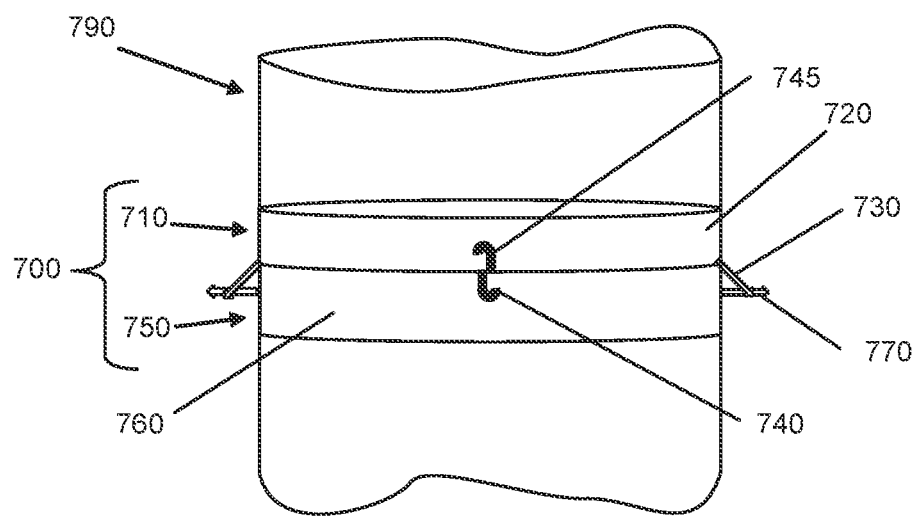

Reference is now made to FIGS. 7A and 7B, which are perspective view simplified illustrations of a graft securing system in accordance with some embodiments of the invention. As shown in FIGS. 7A and 7B, the system comprises two ring-shaped frames 710 and 750, each comprising a plurality of anchors 730/770 protruding radially outwards from frame rings 720/760 and configured to penetrate a graft 780 and tissue (e.g., blood vessel wall) 790 when being urged by radial expansion of the frame rings 720 and 760. In some embodiments, at least one of the frame rings 720/760 has one or more latches 740/745. In some embodiments, at least one of latches 740/745 on a first ring frame is configured to interlock with a respective latch on a second adjacent ring frame when the frame rings 710/750 are axially juxtaposed.

As shown in the exemplary embodiment depicted in FIGS. 7A and 7B, anchors 730/770 protrude in various angles from their respective frame rings 710/750. For example, anchors 770 are perpendicular to a plane defined by a circumferential opening of ring 750, and anchors 730 are angled in respect to a plane defined by a circumferential opening of ring 710. In some embodiments, at least on of anchors 730/770 of at least one of frame rings 720/760 extends towards one or more anchors 730/770 of an adjacent frame ring, thereby, upon deployment of frame rings 720/760 anchors 730/770 of deployed frame rings 720 and 760 interlock. A potential advantage of this configuration is in that interlocked anchors support each other and prevent axial movement of the secured system 700. In some embodiments the anchors of at least one ring 730/770 protrude in varying angles to the axis of the ring 730/770.

Figure 8A:
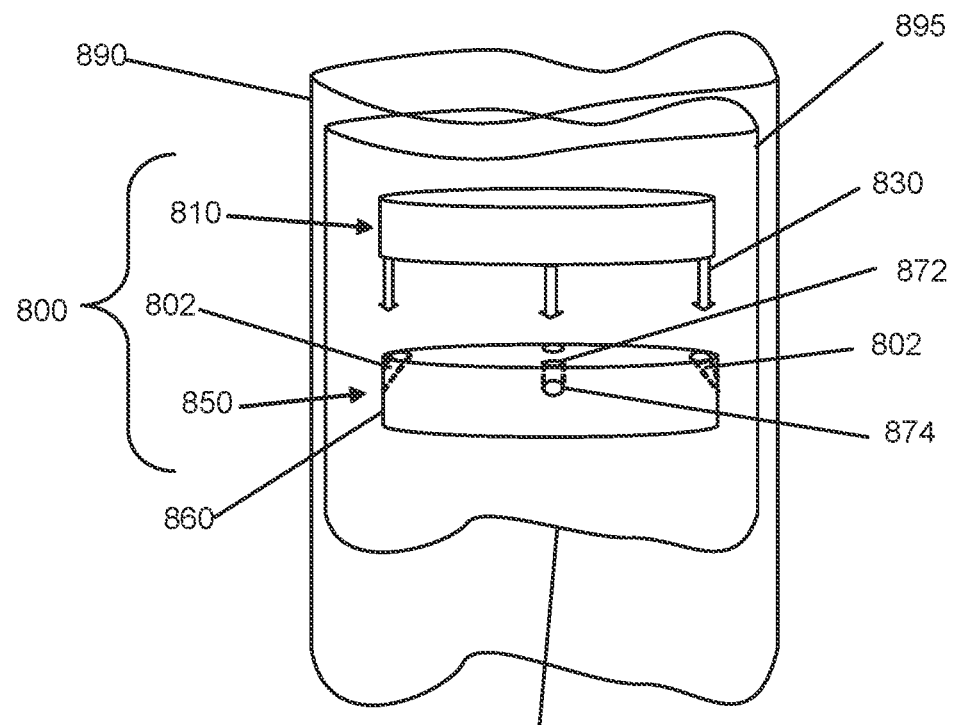
FIGS. 8A and 8B are perspective view simplified illustrations of a graft securing system in accordance with some embodiments of the invention.
Figure 8B:
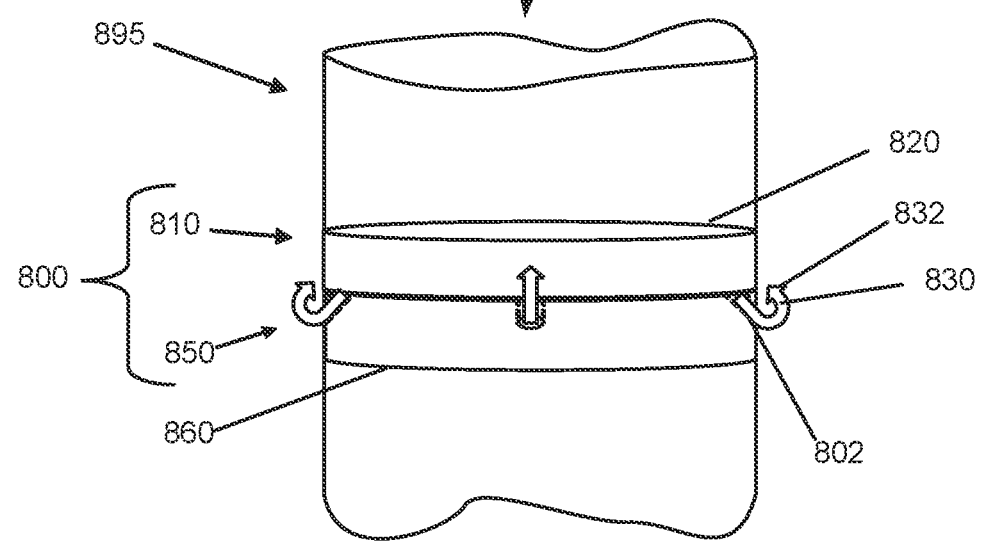

Turning to FIGS. 8A and 8B, which are perspective view simplified illustrations of a graft securing system in accordance with some embodiments of the invention. As shown in FIGS. 8A and 8B, the system comprises: a radially expandable base frame 810 shaped as a ring, and a radially expandable guiding frame 850 shaped as a ring. In some embodiments, at least one of the frames 810/850 are collapsible. In some embodiments, the base frame 810 comprises a plurality of anchors 830 protruding generally perpendicular to a plane defined by a circumferential opening of ring 810. In some embodiments, guiding frame 850 comprises a plurality of guiding channels 802 disposed at the ring wall 860.

The guiding channels 802 are formed generally perpendicular to a plane defined by a circumferential opening of the frame 850 and comprise an entry port 872 and an exit port 874. Anchors 830 connect a tissue (e.g., blood vessel wall) 890 to a graft 880 by penetrating the graft 895 and tissue 890 after passing through guiding channels 802 when the base ring 810 and guiding ring 850 are axially juxtaposed. At least one of frames 810 and 850 is expandable from a retracted state (e.g., within the applicator) to an expanded state in which the frame 850 engages graft 895.

Anchors 830 are shaped and directed into the graft 895 and tissue 890 by guides 802. As shown in FIG. 8B, guiding channels 802 are angled in respect to frame 850 wall and guide the anchors 830 to bend at an angle and receive a post-penetration angled configuration during their deployment through the guides 802. The anchors 830 are deployed within the guiding channels 802 by entering through entry port 872 and existing through exit port 874 during an axial displacement of at least one of the frame 810/850 toward the other 850/810 until frames 810/850 are juxtaposed. In some embodiments as shown in FIG. 8B, the anchors 830 are resilient and are made of a shape memory material e.g. Nitinol.

In some embodiments, the anchors 830 are pre-shaped and assume a pre-shaped unrestrained configuration when not being restrained. In some embodiments, the anchors 830 are held in a restrained position by a restraining sleeve (not show) prior to entering the anchor guide 870 formed at the guide frame 850. In some embodiments, the anchors 830 are formed according to anchors embodiments explained elsewhere herein (e.g. FIGS. 2A to 5). In some embodiments, when entering guides 802, an anchor restraining sleeve slides away of the distal tip 832 of the anchor 830, so that the anchors 830 assume an unrestrained state upon exiting the guiding channels 802 through port 874. Thereby, when penetrating the graft 895 and the tissue 890, anchors 830 connect the tissue 890 to the graft 895 by assuming a secured configuration in which the tip 832 of the anchor 830 is pressed on the tissue. In some embodiments, the restraining sleeves are parallel to the axis of the restraining sleeve frame.

In some embodiments, components of the graft securing system are manufactured from one or more of the following biocompatible materials: Nitinol, Stainless Steel and Polymer. For example, in some embodiments, at least one of the frame, anchors and restraining sleeve are made of metal, e.g., Nitinol or Stainless Steel. In some embodiments, the restraining sleeve is made of a polymer e.g., Ethylene Propylene Diene Monomer (EPDM), Polytetrafluoroethylene (PTFE) and/or nitrile-butadiene rubber (NBR).

Graft Securing System Applicator

Reference is now made to FIGS. 9A and 9B, which are perspective view, side view and cross section view simplified illustrations of a graft securing system applicator in accordance with some embodiments of the invention. The applicator 1000 comprises: one or more applicator lumens 1400, coupled at a distal end to an applicator head 1200, and at a proximal end to an applicator control handle 1600. As shown in enlarged view A of FIG. 9A and FIG. 9B (section A-A of FIG. 9A), the applicator head 1200 comprises: a head lumen 1280, an applicator tip 1205 disposed at a distal end of the head lumen 1280, a container portion 1202 located proximally to the applicator tip 1205, an axially movable container sheath 1220 surrounding the container portion 1202, a graft securing system 1100 frame 40 holder and driver 1240 carrying a balloon 1300 and graft securing frame 1100, and an frame 1100 releasing sheath 1230 arranged between graft releasing frame 1100 and movable container sheath 1220. In some embodiments, balloon 1300 is a non-compliant balloon. In some embodiments, balloon 1300 is a compliant balloon. In some embodiments, balloon 1300 is a semi-compliant balloon. In some embodiments, holder and driver 1240 comprises a lumen sized to receive a guide wire. In some embodiments, applicator 1000 is guided over the guide wire to a target location for deployment.

In some embodiments, applicator 1000 comprises a resilient protective layer 1302 covering at least a portion of balloon 1300. In some embodiments, protective layer 1302 comprises a sleeve. In some embodiments, protective layer 1302 comprises a balloon. In some embodiments, protective layer 1302 is made of a biocompatible material e.g., fabric, nitinol mesh, nylon, silicone or any other suitable material. In some embodiments, protective layer 1302 is between 0.05-0.6 mm in thickness. A potential advantage in protective layer is in that it protects balloon 1300 from coming into contact with sharp edges of frame 40 or anchors 100 and being damaged or punctured. In some embodiments, the graft securing system 1100 is one of the graft securing systems described elsewhere herein. In some embodiments, prior to applying the graft securing system 1100 by the applicator 1000, system 1100 is fitted within the container portion 1202 at a maximally folded state. In some embodiments, a graft envelops one of the graft securing systems described elsewhere herein disposed at a retracted state. At the maximally retracted state, the graft securing system 1100 is folded, so that the penetration tip of anchors 100 (not shown) is disposed on graft securing system 1100 directed axially distally towards a tip of the dispenser. In some embodiments, when the securing system is released and expanded to an expanded state, the anchors disposed on the graft securing system 1100 are directed radially outwards towards to the graft and the tissue (e.g., blood vessel wall).

In some embodiments, all anchors 100 are biased together by the frame 40 e.g., as shown in FIGS. 1A to 1C. In cases in which frame 40 is re-collapsed into the retracted state (e.g., repositioning) and re-covered with releasing sheath 1230, movement distally (axially forward) of releasing sheath 1230 urges anchors 100 radially centrally into the retracted state in which anchors 100 to point again generally axially, in respect to frame 40.

Reference is now made to FIGS. 9A, 10A and 10B and 11A-D. In some embodiments, a container portion 1202 sheath 1220 is axially movable over container 1202 to assume the following applicator head 1200 states:

1) A closed state (FIGS. 9A-B) in which the container sheath 1220 covers the container 1202 and has a distal rim 1222 adjacent the tip 1205, 2) A partially open state (FIG. 10A) in which the container sheath 1220 is partially retracted proximally, thereby partially exposing the container 1202 and the graft securing system 1100 fitted within the container 1202, and 3) An open state (FIG. 10B) in which the container sheath 1220 is fully retracted proximally fully exposes the frame securing system 1100.

In some embodiment, the applicator head 1200 transitions from a closed state to an open state and vice versa, by sliding the container sheath 1220 axially distally over the container 1202 or axially proximally exposing the container 1202.

In some embodiments of the invention, the frame 40 is locked onto a frame 40 holder and driver 1240 until the frame 40 is unsheathed and exposed. In some embodiments, the frame 40 is unlocked when being unsheathed of the container sheath 1220. In some embodiments, as shown in in FIG. 10B, frame 40 holder and driver 1240 comprises one or more of frame 40 holding pins 1235 disposed circumferentially at an external surface 1242 of the holder and driver 1240. In some embodiments, frame 40 comprises one or more holes 1275 at a proximal end of a frame 40 (e.g., frame 40) sized to fit over and receive holding pins 1235. In some embodiments, the frame 40 is axially locked to the frame 40 holder and driver 1240 by one or more of the pins 1235. In some embodiments, the frame 40 is fitted on the pins 1235 by mounting a proximal pin holes formed at a distal end of frame 40, so that an axial movement or full expansion of the frame 40 is prevented until the frame 40 is released of the pins 1235.

In some embodiments, the applicator head 1200 comprises an axially movable releasing sheath 1230, having a closed state (10A) in which the releasing sheath 1230 is positioned over the holding pins 1235, a partially open state (FIG. 11B) and an open state (FIGS. 10C and 11D) in which the releasing sheath 1230 is retracted proximally and exposes the holding pins 1235. In some embodiments, re-sheathing the frame 40 by either one of the releasing sheath 1230 or the container sheath 1220 is enabled when the frame 40 is locked within the applicator head 1200.

Figure 10A:
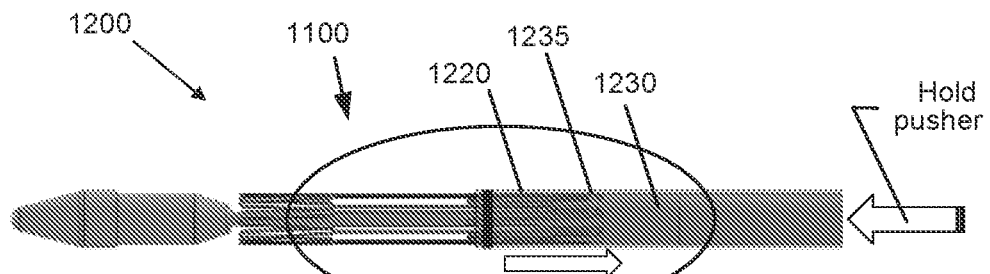
FIGS. 10A and 10B are side view simplified illustrations of a graft securing system delivery device for in accordance with some embodiments of the invention.
Figure 10B:
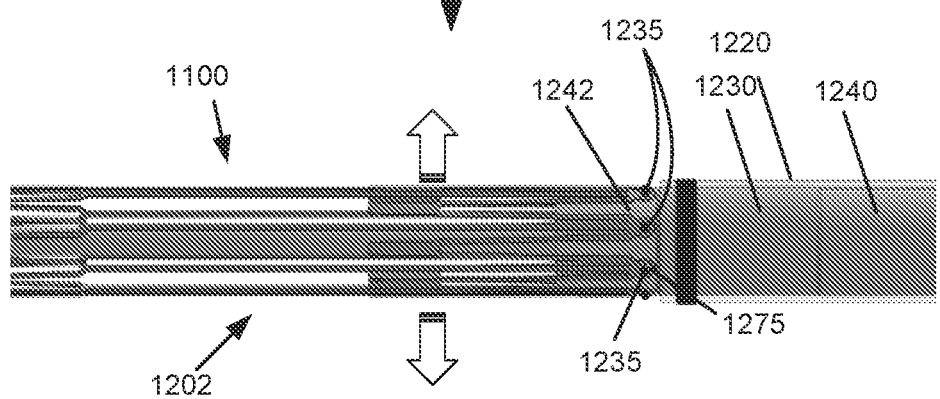

In some embodiments as shown in FIGS. 9A-B, the frame 40 is expandable by a balloon 1300 disposed in lumen 1280 and fixed to holder and driver 1240 and enveloped by frame 40. In some embodiments, the balloon 1300 is inflatable via the lumen 1280 or, in some embodiments, via a space created by adding additional sheath around 1280. In some embodiments as shown in FIGS. 10A, 10B, the frame 40 is folded over the balloon 1300 disposed at a deflated state within the container 1202 prior to applying the frame 40. In some embodiments, balloon 1300 is a non-compliant balloon.

In some embodiment, the method of delivery and the application of the frame 40 by the applicator 1000 comprises:

a) Positioning the applicator head 1200 at the deployment site within a blood vessel. In some embodiments, a marker 1210 disposed at the tip 1205 assists in the initial positioning of the applicator head.

b) Partial unsheathing of the frame 40 by proximally retracing the container sheath 1260 from the distal end 1200 frame 40 partially expands assuming a partially open state.

c) Verifying positioning of frame 40 within the blood vessel.

d) Optionally re-sheathing frame 40 by sliding container sheath 1260 distally over frame 40 so that the head 1200 re-assumes a closed state and repositioning graft securing system 1100 if required followed by repeating stages (1) to (3) Unsheathing the securing system 1100, by retracting the container sheath 1260 so that the head 1200 assumes a partial open state and the securing system is free to expand within the treatment site.

e) Release the securing system from locking pins 1235 by retracting the releasing sheath 1230 to a fully open state.

f) Inflating an actuating balloon 1300 and expanding the frame 40. Urging frame 40 against the graft and/or tissue, thereby securing the graft to the tissue (e.g., blood vessel wall).

Releasing applicator by deflating balloon 1300, re-sheathing with sheath 1230 and 1220, retracting applicator out of the treatment site. Reference is now made to FIGS. 11A, 11B, 11C and 11D, collectively referred to as FIG. 11, which are cross section view simplified illustrations of implementation of a graft securing system applicator device 2000 in accordance with some embodiments of the invention.

In some embodiments, as shown in FIG. 11, the applicator 2000 comprises an applicator head 2200 and an axially movable balloon 2760 and positioned within head 2200 distally to a graft securing system 2100 disposed within the applicator 2000 head 2200. In some embodiments, applicator 2000 comprises a handle coupled over a dedicated wire or carrier and a frame on the handle configured control axially moveable balloon 2760 via the handle frame. In some embodiments, balloon 2760 is inflatable or deflatable via a conduit 2765. In some embodiments, balloon 2760 and frame 40 are arranged concentrically. In some embodiments, balloon 2760 is positioned distally (closer to the applicator tip) to frame 40 and axially slidable towards and away from frame 40.

In some embodiments, the frame 40 is made of self-expanding shape memory material and configured to at least partially self-expand as the outer sheath 1230 is proximally moved by the handle of securing system 2100.

An exemplary method of deployment and application of the graft securing system 1100 by applicator 2000 is depicted in FIG. 11. For simplicity of explanation, the embodiment depicted in FIG. 11 is shown in general outlines and some components of applicator 2000 have been removed altogether.

To better understand the following explanation of operation of applicator 2000 as disclosed in the exemplary embodiment depicted in FIG. 11, the arrangement of applicator 2000 head 2200 components from inside outwards is as follows:

a) Guide wire lumen 2763 configured to receive at least one guidewire (not shown) and, optionally, balloon inflation lumen 2765. In some embodiments, and as shown in FIG. 11, guide wire lumen 2763 and balloon inflation lumen 2765 are collocated adjacent to each other along at least a portion of their length;

b) At least one balloon;

c) One or more balloon inflation/deflation lumina 2765, optionally slidable over guidewire lumen 2763, in which case guide wire lumen 2763 and balloon inflation lumen 2765 are coaxial. In some embodiments, balloon inflation/deflation lumen 2765 and guide wire lumen 2763 are located in separate locations along container portion 1202 and are disposed generally along each other;

d) frame 40 holder and driver 1240, configured to support and hold frame 40 (e.g., in a retracted-closed state) and/or drive frame 40 out of or into applicator 2000 during deployment; and e) releasing sheath 1230 slidable over frame 40 as explained elsewhere herein.

As shown in the exemplary embodiment depicted in FIG. 11, and explained in detail herein, graft securing system 1100 comprises at least two actuating elements: frame 40 and balloon 2760. In some embodiments, one or more components is configured to move along the guide wire. In some embodiments, balloon lumen 2765 is axially and controllably moveable in respect to frame 40 and over guidewire lumen 2763. In some embodiments, moving balloon lumen 2765 translates balloon 2760 towards (proximally) or away from (distally) frame 40.

Once at least a distal portion of frame 40 is at least partially expanded as explained elsewhere herein, applicator device 2000 is configured to move the balloon 2760, still at a deflated state axially proximally to be disposed within the interior of the graft securing system 2100 at least partially expanded portion (e.g. by a wire 2730). In some embodiment, inflating the balloon 2760 positioned within the graft securing system 2100 expands the graft securing system, such that it secures a graft to a blood vessel wall as described elsewhere herein. A potential advantage of a configuration of the applicator 2000 as shown in FIG. 11 is in that the balloon 2760 and the graft securing system 2100 are mounted in tandem requiring less radial space and reducing the external diameter of the applicator head 2200 e.g., to fit within a catheter tube.

In some embodiments the applicator 2200 is configured to enable a re-sheathing of graft securing system 2100 by moving the container sheath 1220 distally. In some embodiments, the applicator 2200 comprises an unsheathing lock, which is provided, for example as a latch, pin, ring, wire, etc. The unsheathing lock is configured to prevent a premature unsheathing of the securing system 1100. In some embodiments, the container sheath 1220 is movable by a nut on the applicator controlling handle 1600.

Figure 11A:
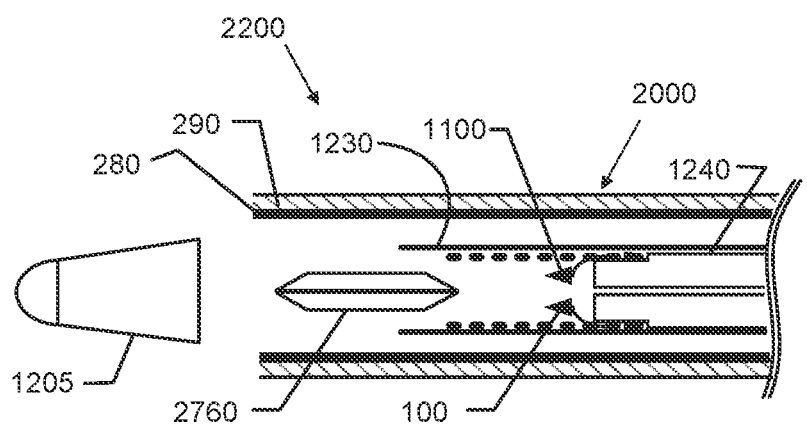
FIGS. 11A, 11B, 11C and 11D are cross section view simplified illustrations of a graft securing system delivery device in accordance with some embodiments of the invention.
Figure 11B:
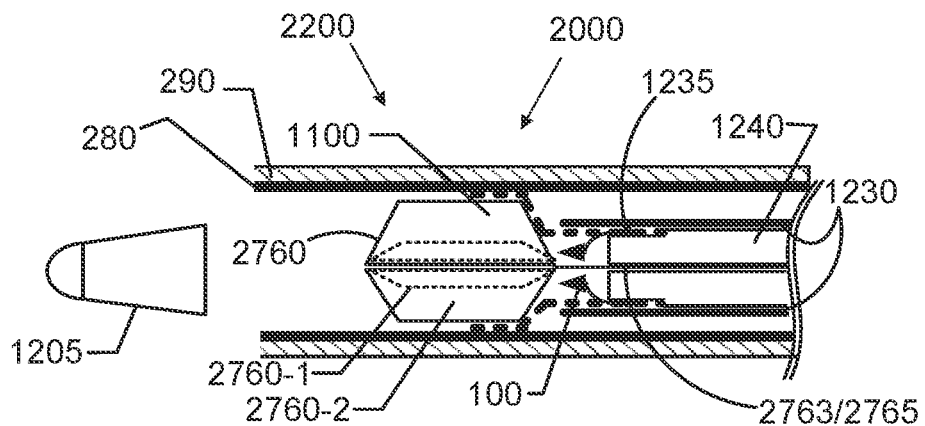

As shown in FIG. 11A, prior to deployment, axially movable balloon 2760 is positioned distally to frame 40, between frame 40 and applicator tip 1205. Anchors 100 are urged centrally, radially centrally and held in place by releasing sheath 1230. The method of deployment of frame 40 comprises, as depicted in FIG. 11B, moving axially movable balloon 2760 in a deflated state 2760-1 axially proximately and positioning balloon 2760 within a distal portion of frame 40 distally to anchors 100. Concurrently or consecutively partially retracting releasing sheath 1230 and allowing self-expansion of a distal portion of frame 40. Expanding axially movable balloon 2760 from a deflated state 2760-1 to an expanded state 2760-2 and urging the partially expanded distal portion of frame 40 against graft 280 and blood vessel wall 290.

At this point the method comprises verifying the deployment location and orientation of frame 40 in respect to blood vessel wall 290.

Figure 11C:
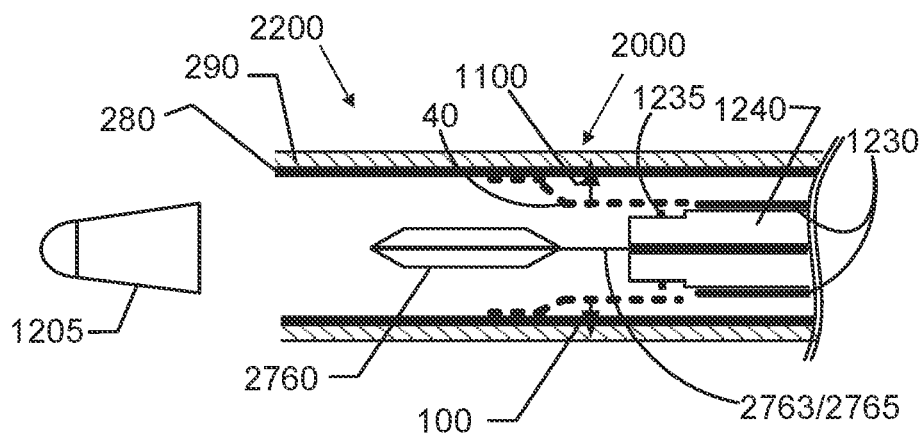

As depicted in FIG. 11C, the method of deployment is continued by deflating axially movable balloon 2760 and concurrently or consecutively fully retracting releasing sheath 1230. Fully retracting releasing sheath 1230 releases support struts 45 that retain their original erect configuration urging anchors 100 radially outwards and at least partially penetrating graft 280 and blood vessel wall 290. Additionally, fully retracting releasing sheath 1230 releases frame 40 from locking pins 1235 and frees frame 40 to at least partially self-expand.

Figure 11D:
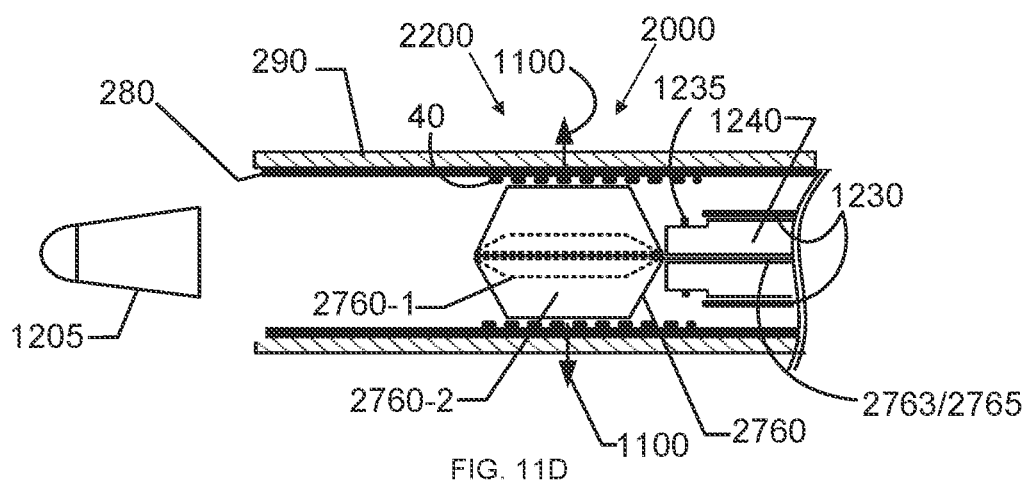

The method is concluded, as shown in FIG. 11D, by expanding axially movable balloon 2760 from a deflated state 2760-1 to an expanded state 2760-2, expanding and urging graft securing system 1100 frame 40 against graft 280 and blood vessel wall 290 fully implanting anchors 100 in place.

In some embodiments of the invention, at least some of the tips of the anchors of the graft securing system 1100 are directed transversely to the graft and/or blood vessel wall after being unsheathed and exposed to the treatment site. In some embodiments (not shown) the applicator head 1200/2200 comprises a plurality of anchor wires, having their tension controllable by the applicator 1000/2000, e.g. through the applicator control handle 1600. The anchor wires are connected at their distal end to a plurality of anchors disposed at the securing system 1100. In some embodiments, one or more anchors disposed on the graft securing system 1100 are selected to be directed toward the graft or the blood vessel wall after the positioning the applicator at the treatment site. In some embodiments, the selected anchors are flexed from a folded state (tips pointing away from the graft/tissue) to a penetration state by a tension applied on the frame 40 or directly on the anchors by the anchor wires. In some embodiments, the balloon is inflated via a dedicated port on the handle of the applicator.

Figure 12:
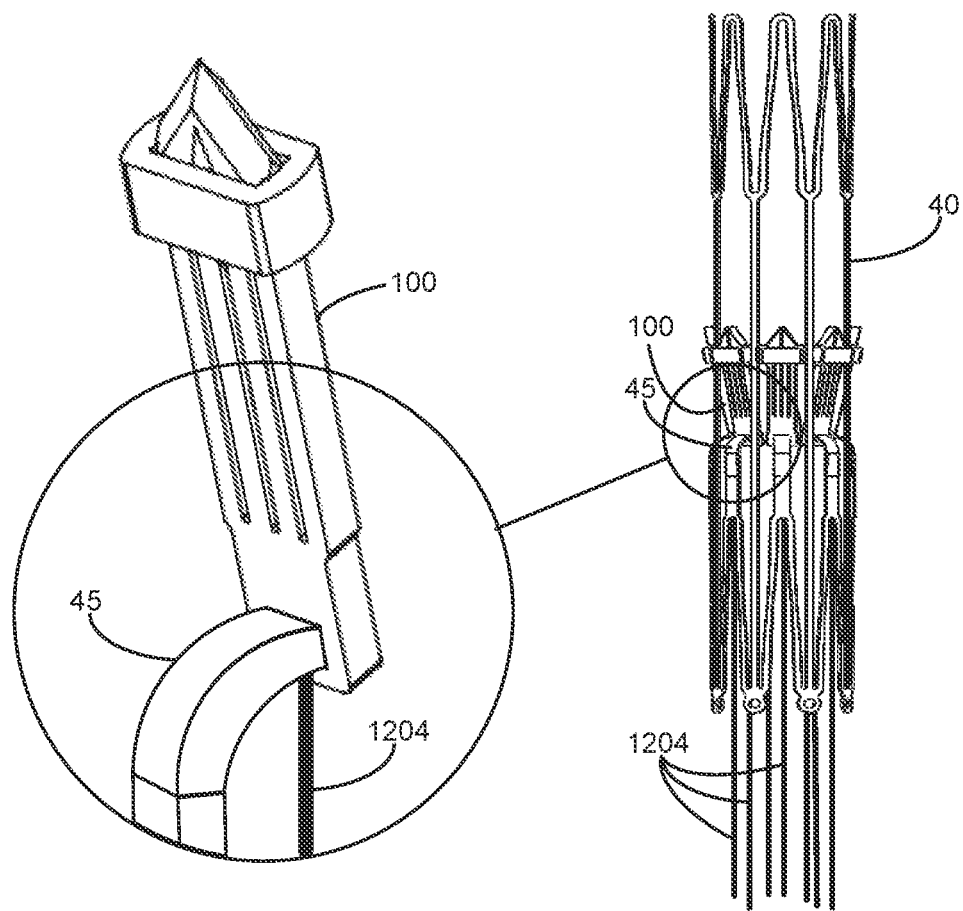
FIG. 12 is a perspective view simplified illustration of an anchor release system of a graft securing system in accordance with some embodiments of the invention.

Referring now to FIG. 12, which is a perspective view simplified illustration of an anchor release system in according to some embodiments of the invention. In some embodiments, movement of support strut 45 from a fully bent (closed) state to a fully straightened (open) state is controlled via a control wire 1204. Control wire 1204 is movable generally axially, the movement controlled by applicator control handle 1600. Axially proximally movement of control wire 1204 places tension on support strut 45 and pulls strut 45 radially centrally into a bent-biased closed state. Alternatively, axially distally movement of control wire 1204 release tension on support strut 45 and enable strut 45 to straighten by moving radially outwards to acquire its preformed shape.

In some embodiments, the shape (e.g., longitudinal cross-section) of frame 40 varies. In some embodiments, the shape of frame 40 is set at the manufacturing stage, e.g., by heat treatment.

Figures 13A, 13B:
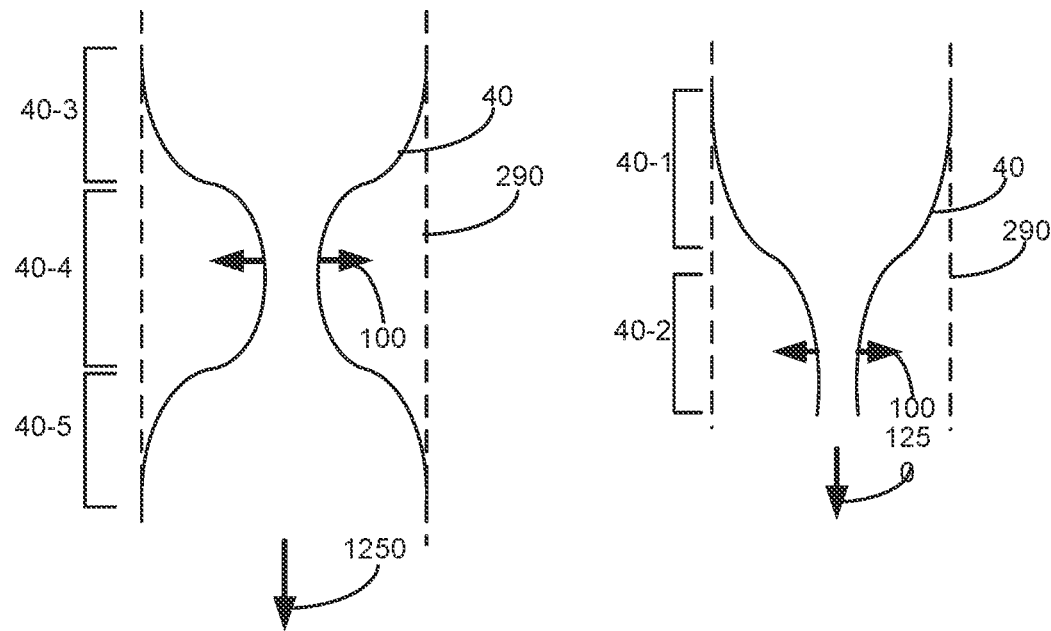
FIGS. 13A, 13B, 13C and 13D are cross-section view simplified illustrations of frame types in according with some embodiments of the current invention.

Reference is now made to FIGS. 13A, 13B, 13C and 13D, which are cross-section view simplified illustrations of frame types in according with some embodiments of the current invention. In some embodiments, and as depicted in FIG. 13A, frame 40 comprises a partially expanded state in which frame 40 assumes a bottle-neck shape. In some embodiments, in the bottle-neck shape proximal portion 40-2 of frame 40 is at least partially collapsed, distal portion 40-1 of frame 40 is expanded sufficiently to come into contact with vessel wall 290 and anchors 100 are extended radially outwards but are distant from and do not contact graft 80/280/612/780/895 and/or vessel wall 290. A potential advantage in this configuration is in that the exact insertion of anchors 100 into the graft 80/280/612/780/895 and/or vessel wall 290 is known and frame 40 can be positioned accordingly in the vessel e.g., by pulling frame 40 proximally as indicated by arrow 1250, without damaging the vessel wall e.g., by anchors 100. In this configuration, a circumference of distal portion 40-1 of frame 40 is in contact with vessel wall 290 maintaining longitudinal stability when frame 40 is moved axially along vessel wall 290.

In the exemplary embodiment depicted in FIG. 13B, Frame 40 comprises an hourglass shaped partially expanded state in which a middle portion 40-4 of frame 40 is at least partially collapsed, proximal 40-5 and distal 40-3 portions of frame 40 are expanded sufficiently to come into contact with vessel wall 290 and anchors 100 are extended radially outwards but are distant from and do not contact graft 80/280/612/780/895 and/or vessel wall 290. A potential advantage in this configuration is in that the exact insertion of anchors 100 into the graft 80/280/612/780/895 and/or vessel wall 290 is known and frame 40 can be positioned accordingly in the vessel e.g., by pulling frame 40 proximally as indicated by arrow 1250, without damaging the vessel wall e.g., by anchors 100. In this configuration, a circumference of both proximal 40-5 and distal 40-3 portions of frame 40 are in contact with vessel wall 290 maintaining.

Figures 13C, 13D:
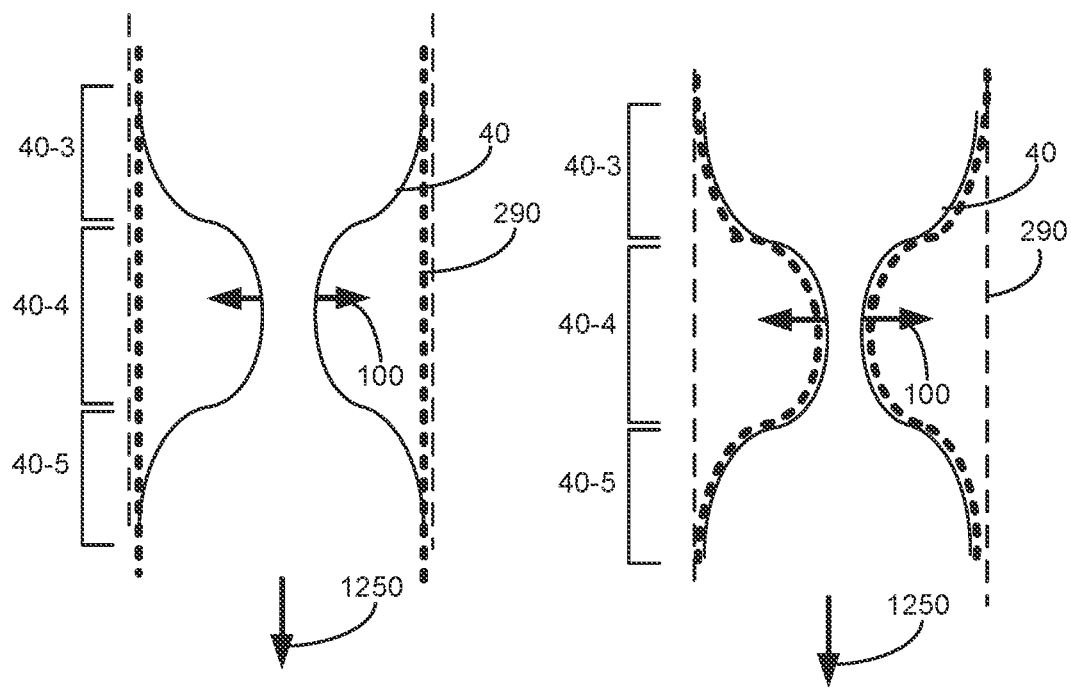

In some embodiments, and as shown in FIGS. 13C and 13D, graft 80/280/612/780/895 follows the shape of frame 40 throughout the length of frame 40 (FIG. 13C). Alternatively, and optionally, in some embodiments, graft 80/280/612/780/895 follows only the shape of proximal 40-5 and distal 40-3 portions of frame 40 (FIG. 13D) and is stretched freely in between gapping the recess formed by portion 40-4 of frame 40.

In all embodiments described herein, once frame 40 is fully expanded, all portions thereof are in direct or indirect (via graft 80/280/612/780/895) contact with vessel wall 290. In some embodiments, expansion of a balloon (e.g., balloon 1300) expands and urges frame 40, throughout its full length directly or indirectly (via graft 80/280/612/780/895) against vessel wall 290.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A tissue anchoring device comprising at least one anchor attached to an expandable frame, said at least one anchor including at least two tissue-penetrating prongs and a restraining sleeve at least partially slideably moveable along said at least two tissue-penetrating prongs, said at least two tissue-penetrating prongs having a first sleeve stop shaped as a rib protruding outwards from said at least two tissue-penetrating prongs and extending beyond an internal cross-section of said restraining sleeve for preventing said restraining sleeve from sliding past a tip of said at least one anchor, wherein moving of said restraining sleeve from a first position where said restraining sleeve restrains said at least two tissue-penetrating prongs at a first configuration for delivery into a tissue, to a second position along said at least two tissue-penetrating prongs releases said at least two tissue-penetrating prongs to deflect in opposite directions at a second configuration for securement to said tissue.

2. The device of claim 1, wherein said at least one anchor is elastically attached to said expandable frame and can be elastically bent from a direction that is generally perpendicular to a longitudinal axis of said frame to a direction that is generally parallel to said longitudinal axis of said frame.

3. The device of claim 2, wherein, when said frame is in an expanded state, said at least one anchor is generally perpendicular to said longitudinal axis of said frame.

4. The device of claim 2, wherein said at least one anchor is attached to said frame through an elastic support strut.

5. The device of claim 4, wherein an end of said support strut fits within a cutout at a base of said at least one anchor.

6. The device of claim 1, wherein said at least two tissue-penetrating prongs are pre-shaped to assume said second configuration where said at least two tissue-penetrating prongs are deflected away from each other.

7. The device of claim 1, wherein, when in said first position, said restraining sleeve maintains said at least two tissue-penetrating prongs juxtaposed throughout their length at said first configuration for delivery into said tissue.

8. The device of claim 7, wherein said at least two tissue-penetrating prongs comprise a buckling preventing lock configured to prevent buckling of said at least one anchor during penetration into said tissue.

9. The device of claim 8, wherein said buckling prevention lock comprises a protrusion extending from a first prong of said at least two tissue-penetrating prongs, and a recess in a juxtaposed second prong of said at least two tissue-penetrating prongs configured to receive said at least one protrusion.

10. The device of claim 1, wherein said at least two tissue-penetrating prongs includes a second sleeve stop, and wherein proximal movement of said restraining sleeve past said second sleeve stop requires a predetermined force.

11. The device of claim 1, wherein said at least two tissue-penetrating prongs comprise two internal prongs positioned between two external prongs.

12. The device of claim 11, wherein said two internal prongs include a blunt tip.

13. The device of claim 1, wherein said frame is self expandable.

14. The device of claim 1, wherein said at least one anchor is positioned between longitudinal struts of said frame.

15. The device of claim 1, wherein said at least one anchor includes two tissue penetration tips.

16. The device of claim 15, wherein each of said two tissue penetration tips of said anchor includes two cutting edges.

17. d) A method of securing a graft to a tissue comprising:
(a) providing a tissue anchoring device including at least one anchor elastically attached to an expandable frame, said at least one anchor including at least two tissue-penetrating prongs and a restraining sleeve at least partially slideably moveable along said at least two tissue-penetrating prongs, said at least two tissue-penetrating prongs having a first sleeve stop shaped as a rib protruding outwards from said at least two tissue-penetrating prongs and extending beyond an internal cross-section of said restraining sleeve for preventing said restraining sleeve from sliding past a tip of said at least one anchor;
(b) collapsing said expandable frame within a delivery catheter such that said at least one anchor is forced in a direction that is generally parallel to a longitudinal axis of said frame;
(c) releasing said device within the graft positioned against a tissue thereby releasing said at least one anchor to elastically move to a direction that is generally perpendicular to said longitudinal axis of said frame;
(d) penetrating a wall of the graft and said tissue via said at least two tissue-penetrating prongs such that said at least two tissue-penetrating prongs transition from a first configuration where said restraining sleeve restrains said at least two tissue-penetrating prongs for delivery into said tissue to a second configuration where said restraining sleeve releases said at least two tissue-penetrating prongs to deflect in opposite directions for securement of said device to the graft and the tissue.

18. The method of claim 17, wherein the tissue is vascular tissue.

19. The method of claim 17, wherein (d) is effected by inflating a balloon within said frame.

20. The method of claim 19, wherein said balloon is at least partially covered by a protective sleeve.

* * * * *

UNITED STATES PATENT AND TRADEMARK OFFICE
CERTIFICATE OF CORRECTION

| | |
|---|---|
| PATENT NO. | : 12,097,136 B2 |
| APPLICATION NO. | : 17/120179 |
| DATED | : September 24, 2024 |
| INVENTOR(S) | : Ron Karmeli and Eyal Teichman |

It is certified that error appears in the above-identified patent and that said Letters Patent is hereby corrected as shown below:

On the Title Page

Related U.S. Application Data, insert -- (60) Provisional application No. 62/684,339, filed on June 13, 2018. --

In the Claims

Column 22, Line 32, delete "d) A method of securing a graft to a tissue comprising:" and insert -- A method of securing a graft to a tissue comprising: --

Signed and Sealed this
Twenty-sixth Day of August, 2025

Coke Morgan Stewart
*Acting Director of the United States Patent and Trademark Office*